US008779134B1

(12) United States Patent
Chi et al.

(10) Patent No.: US 8,779,134 B1
(45) Date of Patent: Jul. 15, 2014

(54) SIX-COORDINATED RUTHENIUM COMPLEX

(71) Applicant: National Tsing Hua University, Hsinchu (TW)

(72) Inventors: Yun Chi, Hsinchu (TW); Fa-Chun Hu, Hsinchu (TW); Sheng-Wei Wang, Hsinchu (TW); Wan-Ping Ku, Hsinchu (TW); Pei-Hua Chen, Hsinchu (TW); Ya-Wan Yang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 14/057,263

(22) Filed: Oct. 18, 2013

(30) Foreign Application Priority Data

Apr. 24, 2013 (TW) .............................. 102114592 A

(51) Int. Cl.
*C07F 15/00* (2006.01)
(52) U.S. Cl.
USPC .......................................................... 546/10
(58) Field of Classification Search
USPC .......................................................... 546/10
See application file for complete search history.

(56) References Cited

U.S. PATENT DOCUMENTS

| 2010/0258175 A1 | 10/2010 | Chi et al. |
| 2011/0277841 A1 | 11/2011 | Chi et al. |

FOREIGN PATENT DOCUMENTS

| TW | 201139453 A1 | 11/2011 |
| TW | I379836 B1 | 12/2012 |

OTHER PUBLICATIONS

Hu et al., "Ruthenium(II) Sensitizers with Bulky Isoquinolinyl Pyrazolate Chelates for High Efficient Dye-Sensitized Solar Cells", National Tsing Hua University, Oct. 26, 2012, 1 page.

Hu et al., "Ruthenium(II) Sensitizers with Bulky Isoquinolinyl Pyrazolate Chelates for High Efficient Dye-Sensitized Solar Cells", Oct. 26, 2012, 1 page.

*Primary Examiner* — Charanjit Aulakh
(74) *Attorney, Agent, or Firm* — Birch, Stewart, Kolasch & Birch, LLP

(57) ABSTRACT

A six-coordinated ruthenium complex is represented by the following formula (I):

$$RuL^1L^2L^3 \qquad (I)$$

wherein $L^1$ represents a 2,2'-bipyridine-based bidentate ligand having at least two functional groups selected from COOH, a carboxylate group and the combination thereof; and $L^2$ and $L^3$ independently represent a 1-(haloalkylpyrazole)-isoquinoline-based bidentate ligand of formula (II) or formula (III).

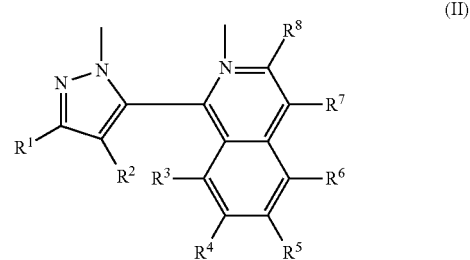

(II)

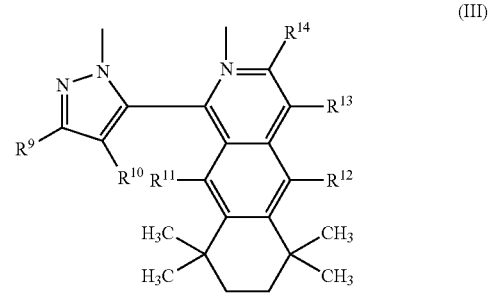

(III)

9 Claims, No Drawings

SIX-COORDINATED RUTHENIUM COMPLEX

CROSS-REFERENCE TO RELATED APPLICATION

This application claims priority of Taiwanese Patent Application No. 102114592, filed on Apr. 24, 2013.

BACKGROUND OF THE INVENTION

1. Field of the Invention

The invention relates to a six-coordinated ruthenium complex which is suitable for use as a dye in a dye-sensitized solar cell, more particularly to a six-coordinated ruthenium complex which includes a 1-(haloalkylpyrazole)-isoquinoline-based bidentate ligand.

2. Description of the Related Art

In recent years, solar cells have been developed with the increasing demand for energy. In particular, the dye-sensitized solar cells have shown most promise among solar cells. The dye-sensitized solar cells absorb visible light and near infrared light to excite electrons. The excited electrons are effectively transferred to a conduction band of a semiconductor electrode in the dye-sensitized solar cells to generate a photocurrent. Therefore, the property of a dye used in the dye-sensitized solar cells would affect directly the photoelectric conversion efficiency of the dye-sensitized solar cell. At present, the ruthenium complex is the main target of research for the dye in the solar cell.

US Patent Application Publication No. 2011/0277841 A1 discloses a photosensitizer represented by the following formula (a):

wherein Ru is ruthenium; X, Y, and Z independently represent a bidentate heterocyclic ligand; X has a structure represented by the following formula (b); Y has a structure represented by the following formula (b), (c), (d), or (e); and Z has a structure represented by the following formula (c), (d), or (e).

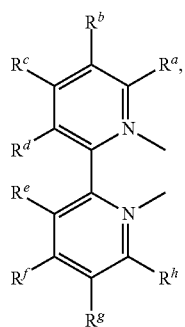

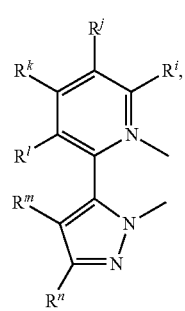

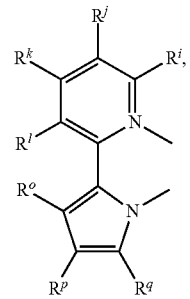

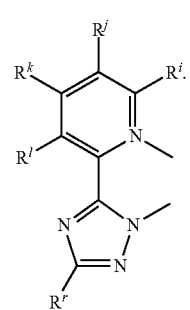

In the formulas (a), (b), (c), and (d), $R^a$, $R^b$, $R^c$, $R^d$, $R^e$, $R^f$, $R^g$, $R^h$, $R^i$, $R^j$, $R^k$, $R^l$, $R^m$, $R^n$, $R^o$, $R^p$, $R^q$, and $R^r$ are independently selected from the group consisting of hydrogen, halogen, an aryl group, an alkenyl group, a $C_1$-$C_{20}$ alkyl group, a cycloalkyl group, an alkynyl group, CN, $CF_3$, an alkylamino group, an amino group, an alkoxy group, a heteroaryl group, a halogen substituted aryl group, a haloalkyl substituted aryl group, a haloalkyl substituted aromatic group, and an aryl substituted $C_1$-$C_{20}$ alkyl group.

In the aforesaid publication, a photosensitizer represented by the following formula (o) is disclosed:

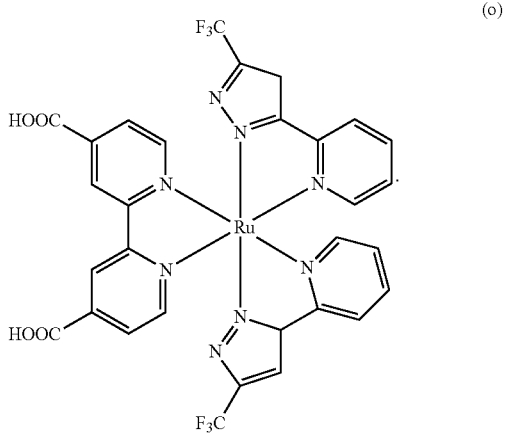

When the photosensitizer of formula (o) is used in the dye-sensitized solar cell, the dye-sensitized solar cell has 12.7 mAcm$^{-2}$ of short circuit current density and 7.84% of photoelectric conversion efficiency. However, the photoelectric conversion efficiency of the conventional dye-sensitized solar cell still cannot satisfy the demand in the industry.

SUMMARY OF THE INVENTION

Therefore, an object of the present invention is to provide a ruthenium complex that can be used in a dye-sensitized solar cell, thereby improving photoelectric conversion efficiency of the dye-sensitized solar cell.

According to the present invention, there is provided a six-coordinated ruthenium complex represented by the following formula (I):

wherein $L^1$ represents a 2,2'-bipyridine-based bidentate ligand having at least two functional groups selected from the group consisting of COOH, a carboxylate group and the combination thereof; and $L^2$ and $L^3$ independently represent a 1-(haloalkylpyrazole)-isoquinoline-based bidentate ligand of formula (II) or formula (III);

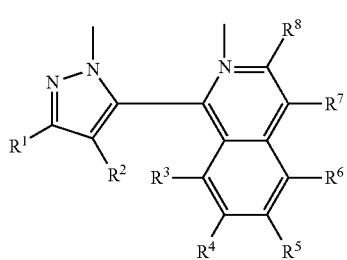

(II)

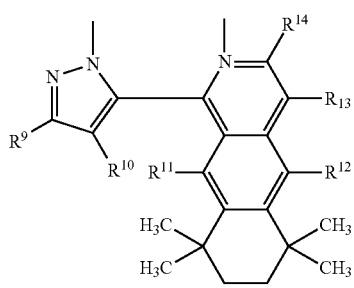

(III)

wherein $R^1$ and $R^9$ independently represent a haloalkyl group; and $R^2$, $R^3$, $R^4$, $R^5$, $R^6$, $R^7$, $R^8$, $R^{10}$, $R^{11}$, $R^{12}$, $R^{13}$, and $R^{14}$ independently represent hydrogen, an isobutyl group, a hexyl group,

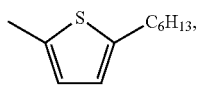

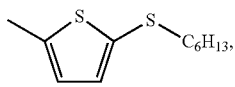

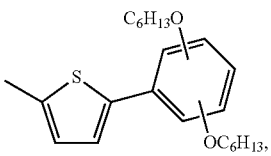

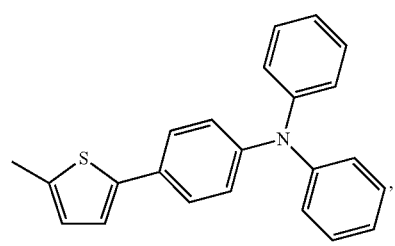

or

DETAILED DESCRIPTION OF THE PREFERRED EMBODIMENTS

This invention provides a six-coordinated ruthenium complex represented by the following formula (I):

$$RuL^1L^2L^3 \quad (I)$$

wherein $L^1$ represents a 2,2'-bipyridine-based bidentate ligand having at least two functional groups selected from the group consisting of COOH, a carboxylate group and the combination thereof; and $L^2$ and $L^3$ independently represent a 1-(haloalkylpyrazole)-isoquinoline-based bidentate ligand of formula (II) or formula (III);

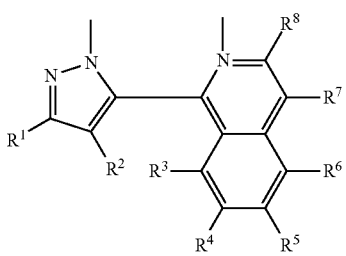

(II)

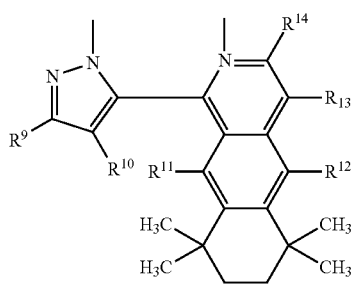

(III)

wherein $R^1$ and $R^9$ independently represent a haloalkyl group; and $R^2$, $R^3$, $R^4$, $R^5$, $R^6$, $R^7$, $R^8$, $R^{10}$, $R^{11}$, $R^{12}$, $R^{13}$, and $R^{14}$ independently represent hydrogen, an isobutyl group, a hexyl group,

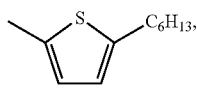

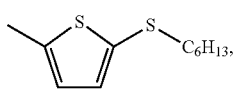

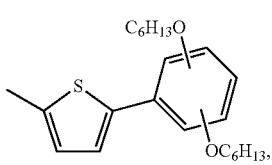

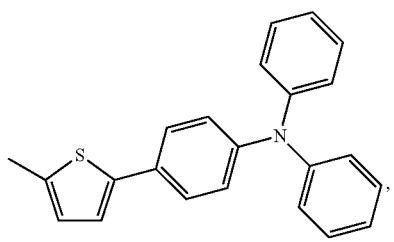 [SMILES: Cc1ccc(-c2ccc(N(c3ccccc3)c3ccccc3)cc2)s1]

or

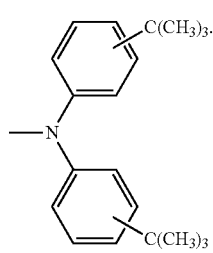

Preferably, $R^1$ and $R^9$ independently represent $C_nF_{2n+1}$, and n represents an integer ranging from 1 to 7.

Preferably, $R^2$, $R^3$, $R^4$, $R^5$, $R^6$, $R^7$, $R^8$, $R^{10}$, $R^{11}$, $R^{12}$, $R^{13}$, and $R^{14}$ independently represent hydrogen, an isobutyl group, a hexyl group,

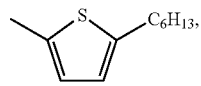

or

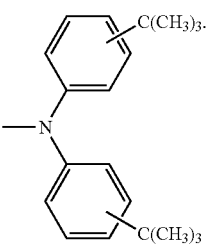

In order to alleviate a π-π stacking effect generated by the isoquinoline that results in the stacking of the six-coordinated ruthenium complex and thereby affects the open circuit voltage of the dye-sensitized solar cell, preferably, $R^3$, $R^4$, $R^5$, $R^6$, $R^7$, and $R^8$ cannot be hydrogen at the same time. Preferably, $R^{11}$, $R^{12}$, $R^{13}$, and $R^{14}$ also cannot be hydrogen at the same time.

In the examples of the present invention, the 1-(haloalkylpyrazole)-isoquinoline-based bidentate ligand of formula (II) is

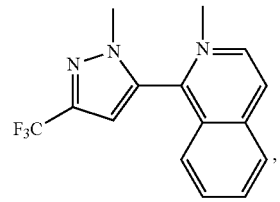

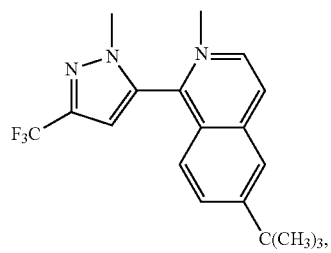

7
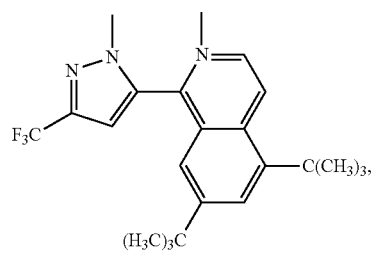
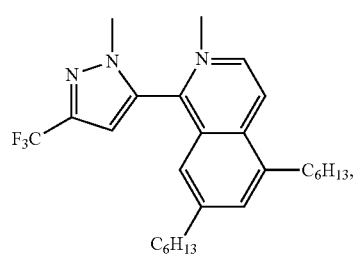
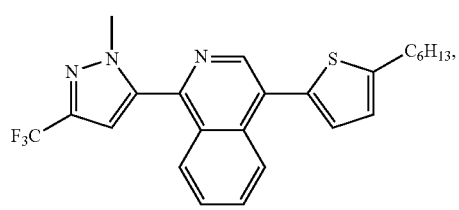
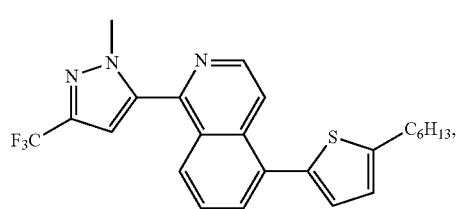
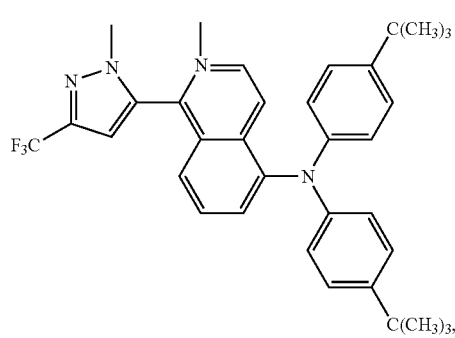
8
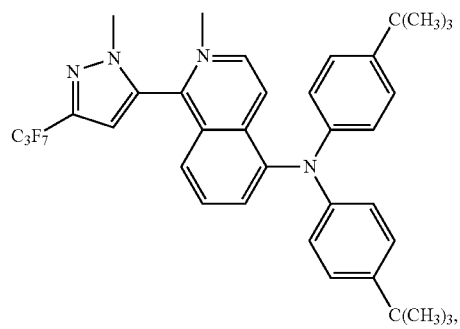
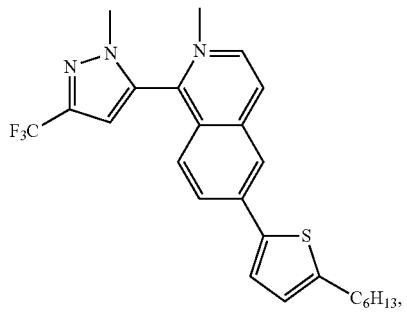
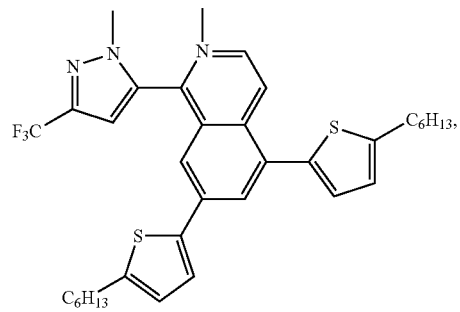
or
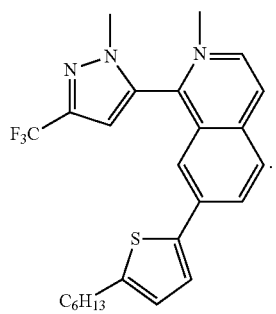
In the examples of the present invention, the 1-(haloalkylpyrazole)-isoquinoline-based bidentate ligand of formula (III) is

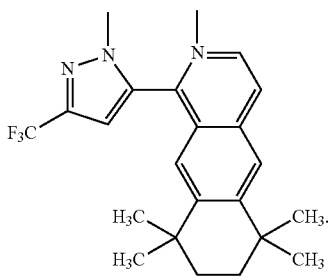

Preferably, the 2,2'-bipyridine-based bidentate ligand is represented by the following formula (IV):

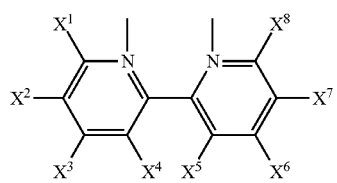

(IV)

wherein $X^1$, $X^2$, $X^3$, $X^9$, $X^5$, $X^6$, $X^7$, and $X^8$ independently represent hydrogen, halogen, a trifluoromethyl group, a $C_1$ to $C_{12}$ linear alkyl group, a $C_1$ to $C_{12}$ branched alkyl group, a phosphoryl group, a phosphate group, a boric acid group, a borate group, a sulfo group, a sulfonate group, a carboxylate group or —COOH; with the proviso that at least two of $X^1$, $X^2$, $X^3$, $X^4$, $X^5$, $X^6$, $X^7$, and $X^8$ represent —COOH, the carboxylate group, or the combination thereof.

Preferably, $X^3$ and $X^6$ independently represent —COOH.

Preferably, $X^3$ and $X^6$ independently represent a carboxylate group.

Preferably, the carboxylate group is represented by —COOM, in which M is a metal ion.

In the examples of the present invention, the 2,2'-bipyridine-based bidentate ligand having at least two —COOH groups of formula (IV) is

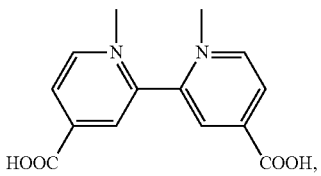

and the 2,2'-bipyridine-based bidentate ligand having at least two carboxylate groups of formula (IV) is

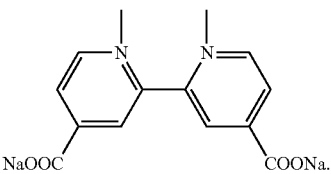

Isoquinoline is used in the present invention to provide extended conjugation to facilitate absorption of the six-coordinated ruthenium complex in a regime ranging from 400 to 600 nm of solar spectrum. Therefore, a short circuit current density of the dye-sensitized solar cell may be increased, and a photoelectric conversion efficiency of the dye-sensitized solar cell may be improved.

The proper reactants and reaction conditions for the six-coordinated ruthenium complex may be selected based on the ligands of the ruthenium complex. It should be noted that, in the chemical formula of the ligand of this invention and the chemical formulas of the reactants used to prepare the ligand of this invention, the same serial number has the same definition. For example, $R^5$ of a reactant (see below) has the same definition as $R^5$ in formula (II) of this invention.

The reaction steps for preparing the six-coordinated ruthenium complex of this invention comprises the following steps of: reacting a 2,2'-bipyridine-based bidentate ligand having at least two functional groups selected from the group consisting of COOH, a carboxylate group, and the combination thereof with a ruthenium source under heating to form a reaction product, and then reacting the reaction product with a 1-(haloalkylpyrazole)-isoquinoline-based bidentate compound represented by formula (V) or (VI) in the presence of a catalyst under heating to form the six-coordinated ruthenium complex of the present invention.

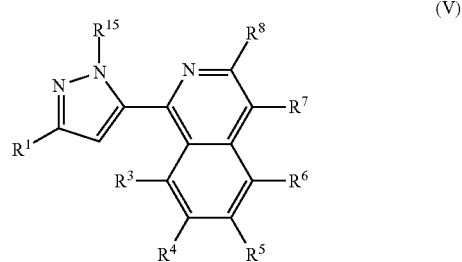

(V)

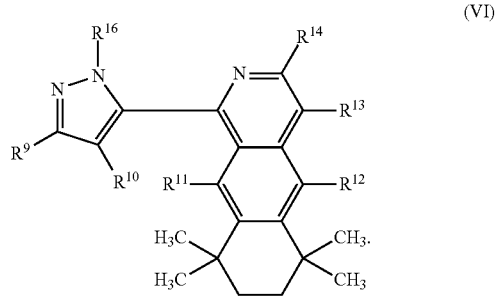

(VI)

In formulas (V) and (VI), $R^1$ and $R^9$ independently represent a haloalkyl group; $R^2$, $R^3$, $R^4$, $R^5$, $R^6$, $R^7$, $R^8$, $R^{10}$, $R^{11}$, $R^{12}$, $R^{13}$, and $R^{14}$ independently represent hydrogen, an isobutyl group, a hexyl group,

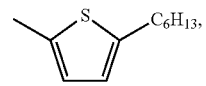

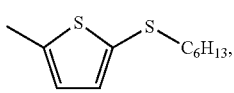

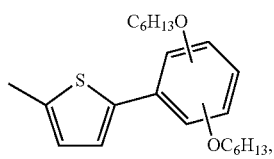

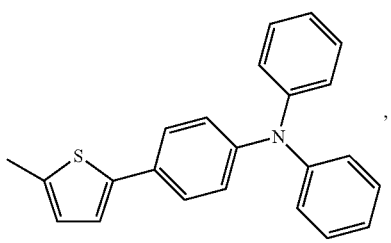 [SMILES: Cc1ccc(-c2ccc(N(c3ccccc3)c3ccccc3)cc2)s1]

or

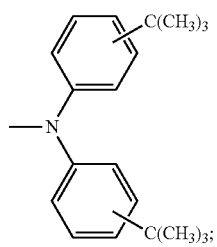

and $R^{15}$ and $R^{16}$ independently represent hydrogen.

Preferably, the 2,2'-bipyridine-based bidentate compound is represented by the following formula (VII):

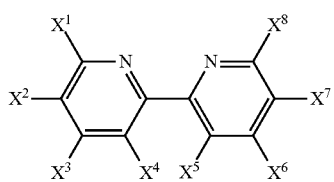

(VII)

wherein $X^1$, $X^2$, $X^3$, $X^4$, $X^5$, $X^6$, $X^7$, and $X^8$ independently represent hydrogen, halogen, a trifluoromethyl group, a $C_1$ to $C_{12}$ linear alkyl group, a $C_1$ to $C_{12}$ branched alkyl group, a phosphoryl group, a phosphate group, a boric acid group, a borate group, a sulfo group, a sulfonate group, a carboxylate group or —COOH; with the proviso that at least two of $X^1$ to $X^8$ represent —COOH, the carboxylate group, or the combination thereof.

Preferably, the ruthenium source is di-μ-chlorobis[(p-cymene)chlororuthenium(II)]([Ru(p-cymene)Cl$_2$]$_2$). Preferably, the catalyst is potassium acetate (KOAc) or sodium acetate.

This invention also provides a dye-sensitized solar cell including:

an electrolytic component;
a first electrode disposed in the electrolytic component and including a transparent conductive substrate and a porous film disposed on a surface of the transparent conductive substrate, the porous film absorbing the abovementioned six-coordinated ruthenium complex; and
a second electrode spaced apart from the first electrode and disposed in the electrolytic component.

The electrolytic component includes, but is not limited to, a mixture solution containing iodine and iodic ions in a solvent containing valeronitrile and acetonitrile (v/v=15: 85).

The transparent conductive substrate is made of a flexible polymer material or a rigid material. The flexible polymer material includes, but is not limited to, polyethylene, polypropylene, polyimide, polymethyl methacrylate, polycarbonate, polyethylene terephthalate, etc. The rigid material includes, but is not limited to, glass. The porous film is made of a material that includes, but is not limited to, titanium dioxide (TiO$_2$), zinc oxide or tin oxide.

The method for manufacturing the dye-sensitized solar cell is well known in the art and will not be described in detail hereinafter.

The present invention will be further described by way of the following examples. It is understood that the following examples are used for illustration, and should not be construed as limiting the implementation of the present invention.

EXAMPLES

Preparation 1

Sodium ethoxide (1.66 g, 24.4 mmol) was placed in a 100 ml two-neck bottle, followed by evacuating and injecting nitrogen gas three times. Next, dehydrated tetrahydrofuran (THF, 70 ml) was added into the two-neck bottle, and a solution obtained by dissolving 2.77 g of 1-acetylisoquinoline in THF was then added therein under an ice bath, followed by stirring for 30 minutes. Ethyl trifluoroacetate (2.9 ml, 24.4 mmol) was then added to obtain a reaction mixture, followed by heating the reaction mixture to room temperature and then further heating under reflux for 12 hours. After the reaction was finished, THF was removed and deionized water (100 ml) was added. Thereafter, hydrogen chloride (2N) was dropwise added into the two-neck bottle to adjust pH of the reaction mixture to about 4 to 5, followed by adding ethyl acetate (EA) (100 ml) for partition extraction. The partition extraction was conducted three times. A collected organic layer was added with anhydrous sodium sulfate (Na$_2$SO$_4$) to remove water, followed by filtration to obtain a filtrate. EA was removed from the filtrate by reduced pressure distillation to obtain a first intermediate.

The first intermediate (4.32 g, 16.2 mmol) and ethanol (50 ml) were added in a 100 ml single neck bottle, followed by adding hydrazine monohydrate (N$_2$H$_4$.H$_2$O, 4.0 ml, 80.9 mmol) to obtain a reaction mixture. After that, the reaction mixture was heated under reflux for 12 hours. After the reaction was finished, ethanol was removed, and partition extraction using EA and water (100 ml) was conducted three times. A collected organic layer was added with anhydrous sodium sulfate to remove water, followed by filtration to obtain a filtrate. EA was removed from the filtrate by reduced pressure distillation to obtain a distilled mixture. The distilled mixture was subjected to column chromatography using an eluent of EA and hexane (EA: hexane=1:2). A white solid product was obtained (2.21 g, 52% yield).

The spectrum analysis for the white solid product is: $^1$H NMR (400 MHz, CDCl$_3$, 298K), δ (PPm): 8.90 (d, J=8.0 Hz, 1H), 8.56 (d, J=13.6 Hz, 1H), 7.83 (d, J=8.0 Hz, 1H), 7.68 (d, J=10.4 Hz, 1H), 7.64 to 7.60 (m, 2H), 6.82 (s, 1H), 1.44 (s, 9H); $^{19}$F NMR (376 MHz, CDCl$_3$, 298K), δ (ppm): −64.48 (s, 3F). The chemical structure of the white solid product is

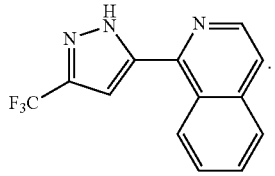 [SMILES: FC(F)(F)c1cc(-c2nccc3ccccc23)[nH]n1]

Preparation 2

Sodium hydride (NaH, 285 mg, 11.9 mmol) was added in a 100 ml two-neck bottle, followed by evacuating and injecting nitrogen gas three times. Next, dehydrated THF (50 ml) was added into the two-neck bottle, and a solution obtained by dissolving 1.5 g of 1-acetyl-6-tert-butylisoquinoline in THF was then added under an ice bath, followed by stirring for 30 minutes. Ethyl trifluoroacetate (2.9 ml, 24.4 mmol) was then added to obtain a reaction mixture, followed by heating the reaction mixture to room temperature and then further heating under reflux for 12 hours. After the reaction was finished, THF was removed and deionized water (100 ml) was added. Thereafter, hydrogen chloride (2N) was dropwise added into the two-neck bottle to adjust pH of the reaction mixture to about 4 to 5, followed by adding methylene dichloride (CH$_2$Cl$_2$, 100 ml) for partition extraction. The partition extraction was conducted three times. A collected organic layer was added with Na$_2$SO$_4$ to remove water, followed by filtration to obtain a filtrate. CH$_2$Cl$_2$ was removed from the filtrate by reduced pressure distillation to obtain a second intermediate.

The second intermediate (2.13 g, 6.61 mmol) and ethanol (50 ml) were added in a 100 ml single neck bottle, followed by adding hydrazine monohydrate (3.2 ml, 66.1 mmol) to obtain a reaction mixture. After that, the reaction mixture was heated under reflux for 14 hours. After the reaction was finished, ethanol was removed, and partition extraction with CH$_2$Cl$_2$ and deionized water (100 ml) was conducted three times. A collected organic layer was added with Na$_2$SO$_4$ to remove water, followed by filtration to obtain a filtrate. CH$_2$Cl$_2$ was removed by reduced pressure distillation to obtain a distilled mixture. The distilled mixture was subjected to column chromatography using an eluent of EA and hexane (EA: hexane=1:2). A white solid product was obtained (1.36 g, 65% yield).

The spectrum analysis for the white solid product is: $^1$H NMR (400 MHz, CDCl$_3$, 298K), δ (ppm): 12.82 (br, NH), 8.48 (d, J=5.6 Hz, 1H), 8.43 (d, J=9.6 Hz, 1H), 7.82~7.75 (m, 2H), 7.66 (d, J=5.6 Hz, 1H), 7.19 (s, 1H), 1.42 (s, 9H) ○ $^{19}$F NMR (376 MHz, CDCl$_3$, 298K), δ (ppm): −62.09 (s, 3F); MS (EI): m/z 319 (M)$^+$. The chemical structure of the white solid product is

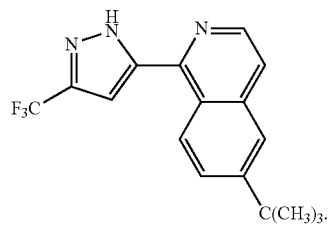

Preparation 3

Sodium ethoxide (1.66 g, 24.4 mmol) was added in a 100 ml two-neck bottle, followed by evacuating and injecting nitrogen gas three times. Next, dehydrated THF (70 ml) was added into the two-neck bottle, and a solution obtained by dissolving 2.77 g of 2-acetylisoquinoline in THF was then added under an ice bath, followed by stirring for 30 minutes. Ethyl trifluoroacetate (2.9 ml, 24.4 mmol) was then added to obtain a reaction mixture, followed by heating the reaction mixture to room temperature and then further heating under reflux for 12 hours. After the reaction was finished, THF was removed and deionized water (100 ml) was added. Thereafter, hydrogen chloride (2N) was dropwise added into the two-neck bottle to adjust pH of the reaction mixture to about 4 to 5, followed by adding EA (100 ml) for partition extraction. The partition extraction was performed three times. A collected organic layer was added with Na$_2$SO$_4$ to remove water, followed by filtration to obtain a filtrate. EA was removed from the filtrate by reduced pressure distillation to obtain a third intermediate.

The third intermediate (4.3 g, 16.2 mmol) and ethanol (50 ml) were added in a 100 ml single neck bottle, followed by adding hydrazine monohydrate (4.0 ml, 80.9 mmol) to obtain a reaction mixture. After that, the reaction mixture was heated under reflux for 12 hours. After the reaction was finished, ethanol was removed, and partition extraction using EA and deionized water (100 ml) was conducted three times. A collected organic layer was added with Na$_2$SO$_4$ to remove water, followed by filtration to obtain a filtrate. EA was removed from the filtrate by means of reduced pressure distillation to obtain a distilled mixture. The distilled mixture was subjected to column chromatography using an eluent of EA and hexane (EA: hexane=1:3). A white solid product was obtained (41% yield).

The spectrum analysis for the white solid product is: $^1$H NMR (400 MHz, CDCl$_3$, 298K), δ(ppm): 11.94 (br, 1H), 8.27 (d, J=8.4 Hz, 1H), 8.08 (d, J=8.0 Hz, 1H), 7.84 (d, J=8.0 Hz, 1H), 7.78-7.69 (m, 2H), 7.57 (t, J=7.6 Hz, 1H), 7.07 (s, 1H); $^{19}$F NMR (376 MHz, CDCl$_3$, 298K), δ (ppm): −62.35 (s, 3F). The chemical structure of the white solid product is

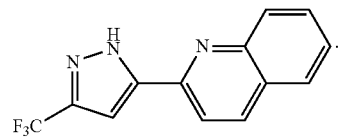 [SMILES: FC(F)(F)c1cc(-c2ccc3ccccc3n2)[nH]n1]

Preparation 4

Potassium tert-butoxide (t-BuOK, 0.15 g, 1.32 mmol) was added in a 100 ml two-neck bottle, followed by evacuating and injecting nitrogen gas three times. Next, dehydrated THF (40 ml) was added into the two-neck bottle, and a solution obtained by dissolving 1.55 g of 2-acetyl-6-tert-butylisoquinoline in THF was then added under an ice bath, followed by stirring for 30 minutes. Ethyl trifluoroacetate (0.2 ml, 1.32 mmol) was then added to obtain a reaction mixture, followed by heating the reaction mixture to room temperature and then further heating under reflux for 12 hours. After the reaction was finished, THF was removed and deionized water (100 ml) was added. Thereafter, hydrogen chloride (2N) was dropwise added into the two-neck bottle to adjust pH of the reaction mixture to about 4 to 5, followed by adding EA (100 ml) for partition extraction. The partition extraction was performed three times. A collected organic layer was added with $Na_2SO_4$ to remove water, followed by filtration to obtain a filtrate. EA was then removed from the filtrate by means of reduced pressure distillation to obtain a fourth intermediate.

The fourth intermediate (2.13 g, 6.61 mmol) and ethanol (50 ml) were added in a 100 ml single neck bottle, followed by adding hydrazine monohydrate (1.7 ml, 34.3 mmol) to obtain a reaction mixture. After that, the reaction mixture was heated under reflux for 24 hours. After the reaction was finished, ethanol was removed, and partition extraction with EA and deionized water (100 ml) was conducted for three times. A collected organic layer was added with $Na_2SO_4$ to remove water, followed by filtration to obtain a filtrate. EA was then removed from the filtrate by means of reduced pressure distillation to obtain a distilled mixture. The distilled mixture was subjected to column chromatography using an eluent of EA and hexane (EA: hexane=1:2). A white solid product was obtained (0.13 g, 46% yield).

The spectrum analysis for the white solid product is: $^1$H NMR (400 MHz, $CDCl_3$, 298K), δ (ppm): 11.63 (br, 1H), 8.20 (d, J=8.4 Hz, 1H), 8.00 (d, J=8.8 Hz, 1H), 7.84 (dd, J=8.8, 2 Hz, 1H), 7.73 (d, J=2.0 Hz, 1H), 7.68 (d, J=8.4 Hz, 1H), 7.04 (s, 1H), 1.42 (s, 9H); $^{19}$F NMR (376 MHz, $CDCl_3$, 298K), δ (ppm): −62.34 (s, 3F); MS (EI): m/z 319 (M)$^+$. The chemical structure of the white solid product is

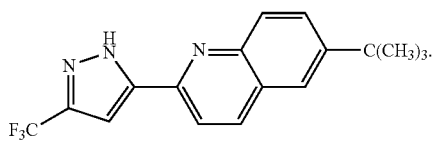 [SMILES: CC(C)(C)c1ccc2nc(-c3cc(C(F)(F)F)n[nH]3)ccc2c1]

Preparation 5

NaH (285 mg, 11.9 mmol) was added in a 100 ml two-neck bottle, followed by evacuating and injecting nitrogen gas three times. Next, dehydrated THF (50 ml) was added into the two-neck bottle, and a solution obtained by dissolving 1.87 g of 1-acetyl-5,7-di-tert-butylisoquinoline in THF was added therein under an ice bath, followed by stirring for 30 minutes. Ethyl trifluoroacetate (2.9 ml, 24.4 mmol) was then added to obtain a reaction mixture, followed by heating the reaction mixture to room temperature and then further heating under reflux for 12 hours. After the reaction was finished, THF was removed and deionized water (100 ml) was added. Thereafter, hydrogen chloride (2N) was dropwise added into the two-neck bottle to adjust pH of the reaction mixture to about 4 to 5, followed by adding $CH_2Cl_2$ (100 ml) for partition extraction. The partition extraction was conducted three times. A collected organic layer was added with $Na_2SO_4$ to remove water, followed by filtration to obtain a filtrate. $CH_2Cl_2$ was removed from the filtrate by means of reduced pressure distillation to obtain a fifth intermediate.

The fifth intermediate (2.5 g, 6.6 mmol) and ethanol (50 ml) were added in a 100 ml single neck bottle, followed by adding hydrazine monohydrate (3.2 ml, 66.1 mmol) to obtain a reaction mixture. After that, the reaction mixture was heated under reflux for 14 hours. After the reaction was finished, ethanol was removed, and partition extraction using $CH_2Cl_2$ and deionized water (100 ml) was conducted three times. A collected organic layer was added with $Na_2SO_4$ to remove water, followed by filtration to obtain a filtrate. $CH_2Cl_2$ was then removed from the filtrate by means of reduced pressure distillation to obtain a distilled mixture. The distilled mixture was subjected to column chromatography using an eluent of EA and hexane (EA: hexane=1:3). A white solid product was obtained (22% yield).

The spectrum analysis for the white solid product is: $^1$H NMR (400 MHz, $CDCl_3$, 298K), δ(ppm): 11.78 (br, NH), 8.48 (d, J=6.2 Hz, 1H), 8.30 (s, 1H), 8.20 (d, J=6.2 Hz, 1H), 7.86 (s, 1H), 7.09 (s, 1H), 1.63 (s, 9H), 1.43 (s, 9H); $^{19}$F NMR (376 MHz, $CDCl_3$, 298K), δ (ppm): −62.20 (s, 3F); MS (EI): m/z 375 (M)$^+$. The chemical structure of the white solid product is

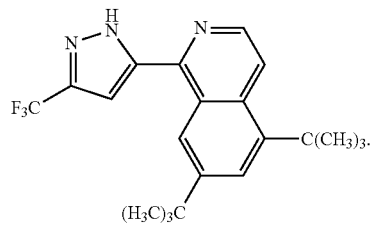 [SMILES: CC(C)(C)c1cc(C(C)(C)C)c2ccnc(-c3cc(C(F)(F)F)n[nH]3)c2c1]

Preparation 6

1,1,3,3,6-pentamethyl-2,3-dihydronaphthalene (9.3 ml, 39.1 mmol) was added in a 500 ml single neck bottle, followed by adding acetic acid (140 ml) and heating to 100° C. A solution obtained by dissolving 5 g of ceric ammonium nitrate in 100 wt % of concentrated acetic acid was dropwise added into the single neck bottle, followed by reaction for 1 hour to obtain a reaction product. After the reaction was finished, the temperature of the reaction product was reduced to room temperature and the reaction product was added with ice cubes (300 g), followed by adding with EA (100 ml) for partition extraction to obtain an organic layer. The organic layer was added with an aqueous solution of sodium carbonate (50 ml, 50 wt %) in an ice bath for neutralization, followed by collecting an organic layer. The organic layer was added with deionized water (100 ml) for partition extraction. The partition extraction was conducted three times. A collected organic layer was added with $Na_2SO_4$ to remove water, followed by filtration to obtain a filtrate. EA was removed from the filtrate by means of reduced pressure distillation to obtain a distilled mixture. The distilled mixture was subjected to column chromatography using an eluent of EA and hexane (EA: hexane=1:15). A light yellow solid product was obtained (77% yield).

The spectrum analysis for the light yellow solid product is: $^1$H NMR (400 MHz, $CDCl_3$, 298K), δ(ppm): 9.93 (s, 1H), 7.81 (d, J=1.6 Hz, 1H), 7.60 (dd, J=8.4, 1.6 Hz, 1H), 7.44 (s, 1H), 7.71 (d, J=8.0 Hz, 1H), 1.70 (s, 4H), 1.31 (s, 6H), 1.29 (s, 6H). The chemical structure of the light yellow solid product is

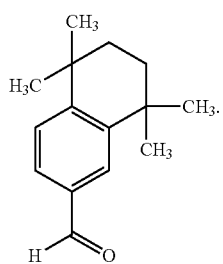

The light yellow solid product (10 g, 61.7 mmol) and amino acetaldehyde dimethyl acetal (6.48 g, 61.7 mmol) were added in a 100 ml single neck bottle, followed by adding toluene (100 ml) to obtain a reaction mixture. After that, a Dean-stark apparatus and a condenser tube were connected to the single neck bottle and the reaction mixture was heated under reflux for 48 hours. After the reaction was finished, toluene was removed and trichloromethane (150 ml) was added into the single neck bottle, followed by maintaining the temperature of the mixture in the single neck bottle at −10° C. Ethyl chloroformate (5.9 ml, 61.7 mmol) and triethyl phosphite (13 ml, 74.1 mmol) were slowly dropwise added into the single neck bottle in sequence, followed by heating to room temperature, stirring at room temperature for 24 hours, and then heating under reflux for 24 hours. Thereafter, the temperature of the mixture in the single neck bottle was lowered to −10° C. and $TiCl_4$ (33.2 ml, 370 mmol) was slowly dropwise added into the single neck bottle. Next, the temperature of the mixture in the single neck bottle was raised to 50° C. and the mixture was stirred at 50° C. for 48 hours. After the reaction was finished, ice cubes (300 g) were disposed in the single neck bottle, followed by taking out an organic layer using a separatory funnel. The organic layer was further subjected to partition extraction using $CH_2Cl_2$ (100 ml) and water (100 ml) for three times. A collected organic layer was added with $Na_2SO_4$ to remove water, followed by filtration to obtain a filtrate. $CH_2Cl_2$ was removed by means of reduced pressure distillation to obtain a distilled mixture. The distilled mixture was subjected to column chromatography using an eluent of EA and hexane (EA: hexane=1:5). A brown oily product was obtained (40% yield).

The spectrum analysis for the brown oily product is: $^1$H NMR (400 MHz, $CDCl_3$, 298K), δ (ppm): 9.13 (s, 1H), 8.37 (d, J=5.6 Hz, 1H), 7.89 (s, 1H), 7.74 (s, 1H), 7.51 (d, J=5.6 Hz, 1H), 1.77 (s, 4H), 1.39 (s, 6H), 1.37 (s, 6H). The chemical structure of the brown oily product is

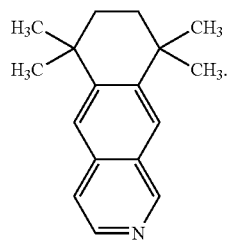 [SMILES: CC1(C)CCC(C)(C)c2cc3cnccc3cc21]

Acetonitrile (100 ml), $FeSO_4 \cdot 7H_2O$ (0.22 g, 0.810 mmol), paraldehyde (33.8 ml, 253 mmol), tert-butyl hydroperoxide (70 wt % aqueous solution, 12.2 ml, 127 mmol), the resultant brown oily product (6.54 g, 50.6 mmol) and trifluoroacetic acid (3.8 ml, 50.6 mmol) were added sequentially in a 250 ml single neck bottle, followed by heating under reflux for 5 hours. Acetonitrile was removed and saturated sodium carbonate aqueous solution was added to conduct a neutralization reaction in an ice bath, followed by extracting using EA so as to obtain an organic layer. The organic layer was added with deionized water for partition extraction, and then an organic layer was collected. The organic layer was added with $Na_2SO_4$ to remove water, followed by filtration to obtain a filtrate. EA was removed from the filtrate by means of reduced pressure distillation to obtain a distilled mixture. The distilled mixture was subjected to column chromatography using an eluent of EA and hexane (EA: hexane=1:5). A yellow-white solid product was obtained (21% yield).

The spectrum analysis for the yellow-white solid product is: $^1$H NMR (400 MHz, $CDCl_3$, 298K), δ (ppm): 8.97 (s, 1H), 8.43 (d, J=5.6 Hz, 1H), 7.76 (s, 1H), 7.69 (d, J=5.6 Hz, 1H), 2.83 (s, 3H), 1.77 (s, 4H), 1.40 (s, 6H), 1.37 (s, 6H). The chemical structure of the yellow-white solid product is

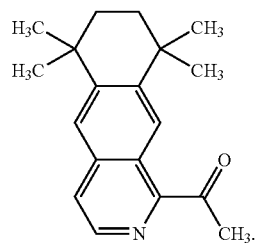 [SMILES: CC(=O)c1nccc2cc3c(cc12)C(C)(C)CCC3(C)C]

NaH (285 mg, 11.9 mmol) was added in a 100 ml two-neck bottle, followed by evacuating and injecting nitrogen gas three times. Next, dehydrated THF (50 ml) was added into the two-neck bottle, and a solution containing 1.7 g of the resultant yellow-white solid product and THF was added therein in an ice bath, followed by stirring for 30 minutes. Ethyl trifluoroacetate (2.9 ml, 24.4 mmol) was then added to obtain a reaction mixture, followed by heating to room temperature and then further heating under reflux for 12 hours. After the reaction was finished, THF was removed and deionized water (100 ml) was added. Thereafter, hydrogen chloride (2N) was dropwise added into the two-neck bottle to adjust pH of the reaction mixture to about 4 to 5, followed by adding $CH_2Cl_2$ (100 ml) for partition extraction. The partition extraction was performed three times. A collected organic layer was added with $Na_2SO_4$ to remove water, followed by filtration to obtain a filtrate. $CH_2Cl_2$ was removed from the filtrate by means of reduced pressure distillation to obtain a sixth intermediate.

The sixth intermediate (2.25 g, 5.95 mmol) and ethanol (50 ml) were added in a 100 ml single neck bottle, followed by adding hydrazine monohydrate (3.2 ml, 66.1 mmol) to obtain a reaction mixture. After that, the reaction mixture was heated under reflux for 14 hours. After the reaction was finished, ethanol was removed, and partition extraction using $CH_2Cl_2$ and deionized water (100 ml) was conducted three times. A collected organic layer was added with $Na_2SO_4$ to remove water, followed by filtration to obtain a filtrate. $CH_2Cl_2$ was removed from the filtrate by means of reduced pressure distillation to obtain a distilled mixture. The distilled mixture was subjected to column chromatography using an eluent of EA and hexane (EA: hexane=1:2). A gray solid product was obtained (56% yield).

The spectrum analysis for the gray solid product is: $^1$H NMR (400 MHz, CDCl$_3$, 298K), δ (ppm): 11.94 (br, NH), 8.40 (d, J=5.2 Hz, 1H), 8.40 (s, 1H), 7.81 (s, 1H), 7.59 (d, J=5.6 Hz, 1H), 7.12 (s, 1H), 1.80 (s, 4H), 1.42 (s, 6H), 1.40 (s, 6H); $^{19}$F NMR (376 MHz, CDCl$_3$, 298K), δ(ppm): −62.14 (s, 3F); MS (EI): m/z 373 (M)$^+$. The chemical structure of the gray solid product is

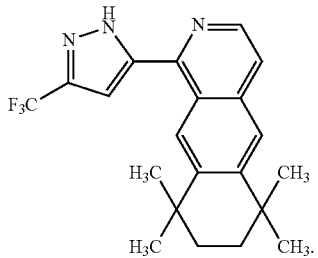 [SMILES: CC1(C)CCC(C)(C)c2cc3c(-c4cc(C(F)(F)F)n[nH]4)nccc3cc21]

Preparation 7

NaH (285 mg, 11.9 mmol) was added in a 100 ml two-neck bottle, followed by evacuating and injecting nitrogen gas three times. Next, dehydrated THF (50 ml) was added into the two-neck bottle, and a solution obtained by dissolving 1.5 g of 1-acetyl-5,7-dihexylisoquinoline in THF was then added under an ice bath, followed by stirring for 30 minutes. Ethyl trifluoroacetate (2.9 ml, 24.4 mmol) was then added to obtain a reaction mixture, followed by heating to room temperature and then further heating under reflux for 12 hours. After the reaction was finished, THF was removed and deionized water (100 ml) was added. Thereafter, hydrogen chloride (2N) was dropwise added into the two-neck bottle to adjust pH of the reaction mixture to about 4 to 5, followed by adding CH$_2$Cl$_2$ (100 ml) for partition extraction. The partition extraction was performed three times. A collected organic layer was added with Na$_2$SO$_4$ to remove water, followed by filtration to obtain a filtrate. CH$_2$Cl$_2$ was removed from the filtrate by means of reduced pressure distillation to obtain a seventh intermediate.

The seventh intermediate (2.87 g, 6.61 mmol) and ethanol (50 ml) were added in a 100 ml single neck bottle, followed by adding hydrazine monohydrate (3.2 ml, 66.1 mmol) to obtain a reaction mixture. After that, the reaction mixture was heated under reflux for 14 hours. After the reaction was finished, ethanol was removed, and partition extraction with CH$_2$Cl$_2$ and deionized water (100 ml) was conducted for three times. A collected organic layer was added with Na$_2$SO$_4$ to remove water, followed by filtration to obtain a filtrate. CH$_2$Cl$_2$ was removed from the filtrate by means of reduced pressure distillation to obtain a distilled mixture. The distilled mixture was subjected to column chromatography using an eluent of EA and hexane (EA: hexane=1:3). A white solid product was obtained (50% yield).

The spectrum analysis for the white solid product is: $^1$H NMR (400 MHz, CDCl$_3$, 298K), δ (ppm): 12.29 (s, 1H), 8.48 (d, J=5.7 Hz, 1H), 8.07 (s, 1H), 7.81 (d, J=5.7 Hz, 1H), 7.44 (s, 1H), 7.14 (s, 1H), 3.02 (t, J=7.6 Hz, 2H), 2.80 (t, J=7.6 Hz, 2H), 1.75~1.66 (m, 4H), 1.41~1.23 (m, 8H), 0.88 (t, J=6.8 Hz, 6H); MS (EI): m/z 432 (M)$^+$. The chemical structure of the white solid product is

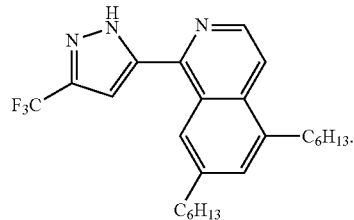

Preparation 8

Sodium ethoxide (0.48 g, 7.05 mmol) was added in a 100 ml two-neck bottle, followed by evacuating and injecting nitrogen gas three times. Next, dehydrated THF (70 ml) was added into the two-neck bottle, and a solution obtained by dissolving 1.6 g of in THF was then added therein under an ice bath, followed by stirring for 30 minutes. Ethyl trifluoroacetate (0.85 ml, 10.6 mmol) was then added to obtain a reaction mixture followed by heating the reaction mixture to room temperature and then further heating under reflux for 12 hours. After the reaction was finished, THF was removed and deionized water (100 ml) was added. Thereafter, hydrogen chloride (2N) was dropwise added into the two-neck bottle to adjust pH of the reaction mixture to about 4 to 5, followed by adding EA (100 ml) for partition extraction. The partition extraction was conducted three times. A collected organic layer was added with anhydrous sodium sulfate (Na$_2$SO$_4$) to remove water, followed by filtration to obtain a filtrate. EA was removed from the filtrate by reduced pressure distillation to obtain an eighth intermediate.

The eighth intermediate (2.32 g, 5.36 mmol) and ethanol (50 ml) were added in a 100 ml single neck bottle, followed by adding hydrazine monohydrate (2.0 ml, 40.9 mmol) to obtain a reaction mixture. After that, the reaction mixture was heated under reflux for 12 hours. After the reaction was finished, ethanol was removed, and partition extraction using EA and water (100 ml) was conducted three times. A collected organic layer was added with anhydrous sodium sulfate to remove water, followed by filtration to obtain a filtrate. EA was removed from the filtrate by means of reduced pressure distillation to obtain a distilled mixture. The distilled mixture was subjected to column chromatography using an eluent of EA and hexane (EA: hexane=1:3). A light yellow solid product was obtained (40% yield).

The spectrum analysis for the light yellow solid product is: $^1$H NMR (400 MHz, CDCl$_3$, 298K), δ (ppm): 11.59 (s, 1H), 8.47 (d, J=5.6 Hz, 1H), 8.47 (d, J=8.4 Hz, 1H), 8.15 (d, J=6 Hz, 1H), 7.80 (d, J=7.2 Hz, 1H), 7.69 (t, J=8.4 Hz, 1H), 7.19 (s, 1H), 7.05 (d, J=3.6 Hz, 1H), 6.87 (d, J=2.8 Hz, 1H), 2.88 (t, J=7.6, 2H), 1.78~1.70 (m, 2H), 1.44~1.32 (m, 6H), 0.90 (t, J=6.9 Hz, 3H); $^{19}$F NMR (376 MHz, CDCl$_3$, 298K), δ (ppm): −58.16. The chemical structure of the light yellow solid product is

21

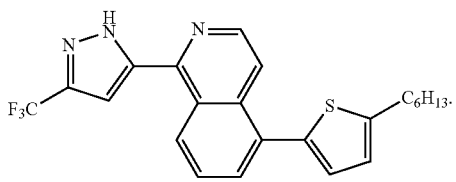

Preparation 9

Sodium ethoxide (0.48 g, 7.05 mmol) was added in a 100 ml two-neck bottle, followed by evacuating and injecting nitrogen gas three times. Next, dehydrated THF (70 ml) was added into the two-neck bottle, and a solution obtained by dissolving 1.6 g of

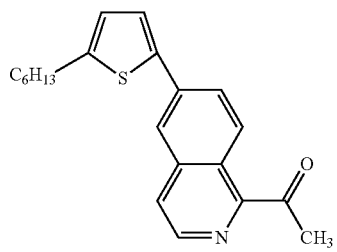

in THF was then added therein under an ice bath, followed by stirring for 30 minutes. Ethyl trifluoroacetate (0.85 ml, 10.6 mmol) was then added to obtain a reaction mixture, followed by heating the reaction mixture to room temperature and then further heating under reflux for 12 hours. After the reaction was finished, THF was removed and deionized water (100 ml) was added. Thereafter, hydrogen chloride (2N) was dropwise added into the two-neck bottle to adjust pH of the reaction mixture to about 4 to 5, followed by adding EA (100 ml) for partition extraction. The partition extraction was conducted three times. A collected organic layer was added with anhydrous sodium sulfate ($Na_2SO_4$) to remove water, followed by filtration to obtain a filtrate. EA was removed from the filtrate by reduced pressure distillation to obtain a ninth intermediate.

The ninth intermediate (2.4 g, 5.54 mmol) and ethanol (50 ml) were added in a 100 ml single neck bottle, followed by adding hydrazine monohydrate (2.0 ml, 40.9 mmol) to obtain a reaction mixture. After that, the reaction mixture was heated under reflux for 12 hours. After the reaction was finished, ethanol was removed, and partition extraction using EA and water (100 ml) was conducted three times. A collected organic layer was added with anhydrous sodium sulfate to remove water, followed by filtration to obtain a filtrate. EA was removed from the filtrate by reduced pressure distillation to obtain a distilled mixture. The distilled mixture was subjected to column chromatography using an eluent of EA and hexane (EA: hexane=1:5). A light yellow solid product was obtained (60% yield).

The spectrum analysis for the light yellow solid product is: $^1$H NMR (400 MHz, $CDCl_3$, 298K), δ (ppm): 12.32 (s, 1H), 8.45 (d, J=5.6 Hz), 8.44 (d, J=9.2 Hz, 1H), 7.96 (s, 1H), 7.91 (d, J=7.6 Hz, 1H), 7.65 (d, J=5.6 Hz, 1H), 7.34 (d, J=3.6 Hz, 1H), 7.20 (s, 1H), 6.82 (d, J=3.6 Hz, 1H), 2.85 (t, J=7.6 Hz, 2H), 1.74~1.70 (m, 2H), 1.40~1.31 (m, 6H), 0.90 (t, J=7.2 Hz, 3H); $^{19}$F NMR (376 MHz, $CDCl_3$, 298K), δ (ppm): −62.11. The chemical structure of the light yellow solid product is

22

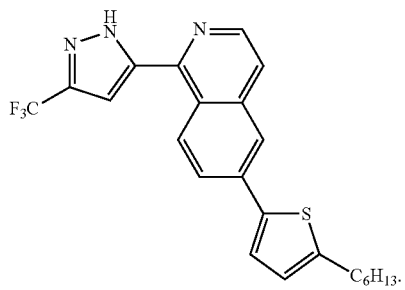

Preparation 10

Sodium ethoxide (0.48 g, 7.05 mmol) was added in a 100 ml two-neck bottle, followed by evacuating and injecting nitrogen gas three times. Next, dehydrated THF (70 ml) was added into the two-neck bottle, and a solution obtained by dissolving 1.6 g of

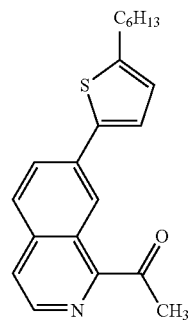

in THF was then added therein under an ice bath, followed by stirring for 30 minutes. Ethyl trifluoroacetate (0.85 ml, 10.6 mmol) was then added to obtain a reaction mixture, followed by heating the reaction mixture to room temperature and then further heating under reflux for 12 hours. After the reaction was finished, THF was removed and deionized water (100 ml) was added. Thereafter, hydrogen chloride (2N) was dropwise added into the two-neck bottle to adjust pH of the reaction mixture to about 4 to 5, followed by adding EA (100 ml) for partition extraction. The partition extraction was conducted three times. A collected organic layer was added with anhydrous sodium sulfate ($Na_2SO_4$) to remove water, followed by filtration to obtain a filtrate. EA was removed from the filtrate by reduced pressure distillation to obtain a tenth intermediate.

The tenth intermediate (2.2 g, 5.4 mmol) and ethanol (50 ml) were added in a 100 ml single neck bottle, followed by adding hydrazine monohydrate (2.0 ml, 40.9 mmol). After that, the reaction mixture was heated under reflux for 12 hours. After the reaction was finished, ethanol was removed, and partition extraction using EA and water (100 ml) was conducted three times. A collected organic layer was added with anhydrous sodium sulfate to remove water, followed by filtration to obtain a filtrate. EA was removed from the filtrate by reduced pressure distillation to obtain a distilled mixture. The distilled mixture was subjected to column chromatography using an eluent of EA and hexane (EA: hexane=1:6). A yellow oily product was obtained (67% yield).

The spectrum analysis for the yellow oily product is: $^1$H NMR (400 MHz, $CDCl_3$, 298K), δ (ppm): 11.98 (s, 1H), 8.56 (s, 1H), 8.49 (d, J=5.6 Hz, 1H), 7.97 (dd, J=8.6 Hz, 1.4 Hz, 1H), 7.87 (d, J=8.6 Hz, 1H), 7.65 (d, J=5.6 Hz, 1H), 7.29 (d, J=3.6 Hz, 1H), 7.23 (s, 1H), 6.83 (d, J=3.5 Hz, 1H), 2.85 (t, J=7.5 Hz, 3H), 1.74~1.70 (m, 2H), 1.56~1.30 (m, 4H), 0.89 (t, J=6.8 Hz, 3H); $^{19}$F NMR (376 MHz, CDCl$_3$, 298K), δ (ppm): −64.05 (s, 3F). The chemical structure of the yellow oily product is

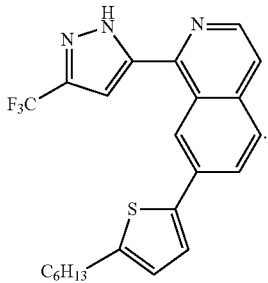

Preparation 11

Sodium ethoxide (0.48 g, 7.05 mmol) was added in a 100 ml two-neck bottle, followed by evacuating and injecting nitrogen gas three times. Next, dehydrated THF (70 ml) was added into the two-neck bottle, and a solution obtained by dissolving 1.6 g of

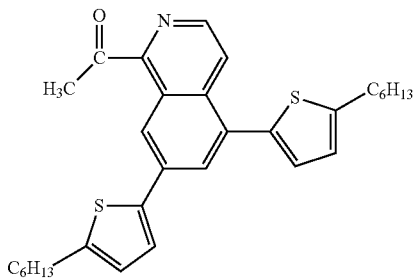

in THF was then added therein under an ice bath, followed by stirring for 30 minutes. Ethyl trifluoroacetate (0.85 ml, 10.6 mmol) was then added to obtain a reaction mixture, followed by heating the reaction mixture to room temperature and then further heating under reflux for 12 hours. After the reaction was finished, THF was removed and deionized water (100 ml) was added. Thereafter, hydrogen chloride (2N) was dropwise added into the two-neck bottle to adjust pH of the reaction mixture to about 4 to 5, followed by adding EA (100 ml) for partition extraction. The partition extraction was conducted three times. A collected organic layer was added with anhydrous sodium sulfate (Na$_2$SO$_4$) to remove water, followed by filtration to obtain a filtrate. EA was removed from the filtrate by reduced pressure distillation to obtain an eleventh intermediate.

The eleventh intermediate (2.6 g, 5.0 mmol) and ethanol (50 ml) were added in a 100 ml single neck bottle, followed by adding hydrazine monohydrate (2.0 ml, 40.9 mmol) to obtain a reaction mixture. After that, the reaction mixture was heated under reflux for 12 hours. After the reaction was finished, ethanol was removed, and partition extraction using EA and water (100 ml) was conducted three times. A collected organic layer was added with anhydrous sodium sulfate to remove water, followed by filtration to obtain a filtrate. EA was removed from the filtrate by reduced pressure distillation to obtain a distilled mixture. The distilled mixture was subjected to column chromatography using an eluent of EA and hexane (EA: hexane=1:5). A yellow solid product was obtained (2.21 g, 60% yield).

The spectrum analysis for the yellow solid product is: $^1$H NMR (400 MHz, CDCl$_3$, 298K), δ (ppm): 11.71 (s, 1H), 8.53 (s, 1H), 8.48 (d, J=5.8 Hz, 1H), 8.07 (d, J=6.0 Hz 1H), 8.01 (s, 1H), 7.30 (d, J=3.5 Hz, 1H), 7.23 (s, 1H), 7.08 (d, J=3.5 Hz, 1H), 6.88 (d, J=3.4 Hz, 1H), 6.82 (d, J=3.4. Hz, 1H), 2.91~2.84 (m, 4H), 1.78~1.68 (m, 4H), 1.41~1.31 (m, 12H), 0.92~0.87 (m, 6H); $^{19}$F NMR (376 MHz, CDCl$_3$, 298K), δ (ppm): −62.11. The chemical structure of the yellow solid product is

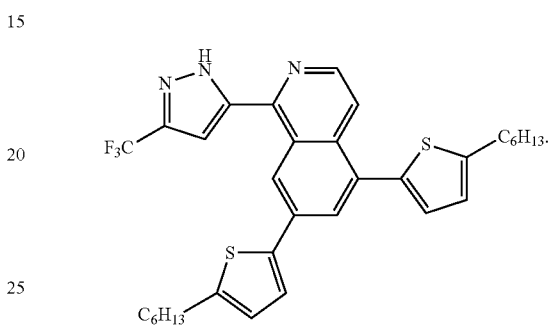

Preparation 12

Sodium ethoxide (80 mg, 1.17 mmol) was added in a 50 ml two-neck bottle, followed by evacuating and injecting nitrogen gas three times. Next, dehydrated THF (15 ml) was added into the two-neck bottle, and a solution obtained by dissolving 350 mg of

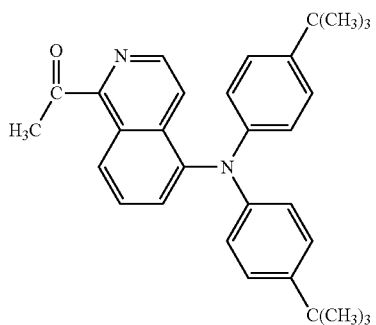 [SMILES: CC(=O)c1nccc2c(N(c3ccc(C(C)(C)C)cc3)c3ccc(C(C)(C)C)cc3)cccc12]

in THF was then added therein under an ice bath, followed by stirring for 30 minutes. Ethyl trifluoroacetate (0.14 ml, 1.17 mmol) was then added to obtain a reaction mixture, followed by heating the reaction mixture to room temperature and then further heating under reflux for 12 hours. After the reaction was finished, THF was removed and deionized water (100 ml) was added. Thereafter, hydrogen chloride (2N) was dropwise added into the two-neck bottle to adjust pH of the reaction mixture to about 4 to 5, followed by adding EA (100 ml) for partition extraction. The partition extraction was conducted three times. A collected organic layer was added with anhydrous sodium sulfate (Na$_2$SO$_4$) to remove water, followed by filtration to obtain a filtrate. EA was removed from the filtrate by reduced pressure distillation to obtain a twelfth intermediate.

The twelfth intermediate (0.43 g, 0.78 mmol) and ethanol (30 ml) were added in a 100 ml single neck bottle, followed by adding hydrazine monohydrate (0.4 ml, 8 mmol) to obtain a reaction mixture. After that, the reaction mixture was heated under reflux for 24 hours. After the reaction was finished, ethanol was removed, and partition extraction using EA and water (100 ml) was conducted three times. A collected organic layer was added with anhydrous sodium sulfate to remove water, followed by filtration to obtain a filtrate. EA was removed from the filtrate by reduced pressure distillation to obtain a distilled mixture. The distilled mixture was subjected to column chromatography using an eluent of EA and hexane (EA: hexane=1:5). A white solid product was obtained (0.24 g, 56% yield).

The spectrum analysis for the white solid product is: $^1$H NMR (400 MHz, CDCl$_3$, 298K), δ(ppm): 8.37 (d, J=5.6 Hz, 1H), 8.31 (d, J=8.4 Hz, 1H), 7.79 (d, J=6 Hz, 1H), 7.64 (t, J=8 Hz, 1H), 7.54 (d, J=7.6 Hz, 1H), 7.21 (s, 1H), 7.20 (d, J=8.4 Hz, 4H), 6.89 (d, J=8.4 Hz, 4H), 1.27 (s, 18H); $^{19}$F NMR (376 MHz, d$_6$-DMSO, 298K), δ(ppm): −62.15 (s, 3F). The chemical structure of the white solid product is

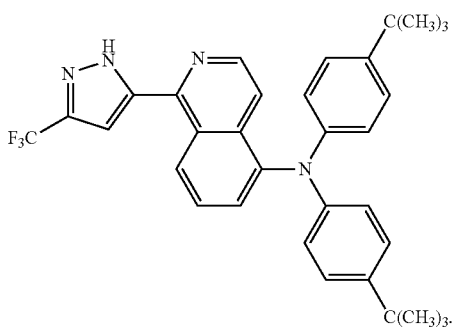

Preparation 13

Sodium ethoxide (80 mg, 1.17 mmol) was added in a 50 ml two-neck bottle, followed by evacuating and injecting nitrogen gas three times. Next, dehydrated THF (15 ml) was added into the two-neck bottle, and a solution obtained by dissolving 350 mg of

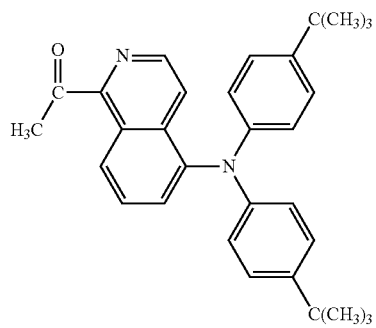 [SMILES: CC(=O)c1nccc2c(N(c3ccc(C(C)(C)C)cc3)c3ccc(C(C)(C)C)cc3)cccc12]

in THF was then added therein under an ice bath, followed by stirring for 30 minutes. Ethyl heptafluorobutyrate (0.14 ml, 1.17 mmol) was then added to obtain a reaction mixture, followed by heating the reaction mixture to room temperature and then further heating under reflux for 12 hours. After the reaction was finished, THF was removed and deionized water (100 ml) was added. Thereafter, hydrogen chloride (2N) was dropwise added into the two-neck bottle to adjust pH of the reaction mixture to about 4 to 5, followed by adding EA (100 ml) for partition extraction. The partition extraction was conducted three times. A collected organic layer was added with anhydrous sodium sulfate (Na$_2$SO$_4$) to remove water, followed by filtration to obtain a filtrate. EA was removed from the filtrate by reduced pressure distillation to obtain a thirteenth intermediate.

The thirteenth intermediate (0.43 g, 0.78 mmol) and ethanol (30 ml) were added in a 100 ml single neck bottle, followed by adding hydrazine monohydrate (0.4 ml, 8 mmol) to obtain a reaction mixture. After that, the reaction mixture was heated under reflux for 24 hours. After the reaction was finished, ethanol was removed, and partition extraction using EA and water (100 ml) was conducted three times. A collected organic layer was added with anhydrous sodium sulfate to remove water, followed by filtration to obtain a filtrate. EA was removed from the filtrate by reduced pressure distillation to obtain a distilled mixture. The distilled mixture was subjected to column chromatography using an eluent of EA and hexane (EA: hexane=1:3). A light yellow solid product was obtained (61% yield).

The spectrum analysis for the light yellow solid product is: $^1$H NMR (400 MHz, CDCl$_3$, 298K), δ (ppm): 8.36 (m, 2H), 7.81 (d, J=5.6 Hz, 1H), 7.67 (t, J=8 Hz, 1H), 7.57 (d, J=7.6 Hz, 1H), 7.21 (d, J=8.4 Hz, 4H), 7.21 (s, 1H), 6.90 (d, J=8.4 Hz, 4H), 1.28 (s, 18H); $^{19}$F NMR (376 MHz, CDCl$_3$, 298K), δ (ppm): −80.20 (t, J=9 Hz, 3F), −110.78 (m, 2H), −127.05 (s, 2H). The chemical structure of the light yellow solid product is

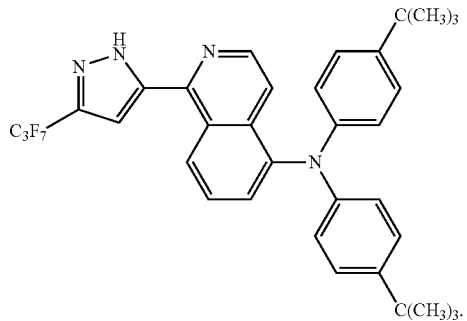

Preparation 14

4,4'-diethoxycarbonyl-2,2'-bipyridine (0.80 g, 2.68 mmol) and [Ru(p-cymene)Cl$_2$]$_2$ (0.82 g, 1.34 mmol) were added in a 150 ml single neck bottle, followed by adding methanol (50 ml) and stirring at 60° C. for 4 hours to obtain a reaction mixture. The temperature of the reaction mixture was lowered to room temperature and a part of methanol was removed. Next, diethyl ether was added into the reaction mixture such that a solid product was precipitated. The solid product was collected using a suction filtration device, followed by washing the solid product using cold methanol and cold diethyl ether, thereby obtaining an orange solid product (0.69 g, 85% yield).

The spectrum analysis for the orange solid product is: $^1$H NMR (400 MHz, CDCl$_3$, 298K), δ (ppm): 10.17 (d, J=5.6 Hz, 2H), 8.64 (s, 2H), 8.28 (d, J=4.8 Hz, 2H), 6.48 (d, J=6.0 Hz, 2H), 6.30 (d, J=6.0 Hz, 2H), 4.48 (q, J=7.2 Hz, 4H), 2.74~2.68 (m, 1H), 1.81 (s, 3H), 1.43 (t, J=7.2 Hz, 6H), 1.03 (d, J=7.2 Hz, 6H). The chemical structure of the orange solid product is

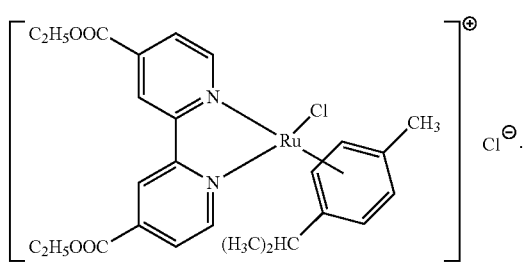

Example 1

The product of Preparation 14 (0.165 mmol), the product of Preparation 1 (0.330 mmol) and potassium acetate (0.824 mmol) were disposed in a 50 ml single neck bottle, followed by adding xylene (20 ml) and heating under reflux for 5 hours. After the reaction was finished, xylene was removed, and the reaction mixture was subjected to partition extraction three times using $CH_2Cl_2$ (50 ml) and deionized water (50 ml). A collected organic layer was added with anhydrous sodium sulfate to remove water, followed by filtration to obtain a filtrate. $CH_2Cl_2$ was removed from the filtrate by means of reduced pressure distillation to obtain a distilled mixture. The distilled mixture was subjected to column chromatography using an eluent of EA and $CH_2Cl_2$ (EA: $CH_2Cl_2$=1:20). A black solid product was obtained (55 mg, 34% yield).

The black solid product (0.0425 mmol) was dissolved in acetone (20 ml), followed by adding sodium hydroxide solution (0.2 ml, 1M) and heating under reflux for 3 hours. After the reaction was finished, acetone was removed and deionized water was added into the reaction mixture. Thereafter, pH of the reaction mixture was adjusted to 3 using hydrogen chloride (2N) so as to precipitate a solid product. The solid product was collected by centrifugation, followed by washing several times with deionized water, acetone and diethyl ether, thereby obtaining a dark brown solid product (30.0 mg, 87% yield).

The spectrum analysis for the dark brown solid product is: $^1$H NMR (400 MHz, $d_6$-DMSO, 298K), δ (ppm): 9.00 (s, 2H), 8.91 (d, J=5.6 Hz, 2H), 8.09 (d, J=5.6 Hz, 2H), 7.94~7.86 (m, 4H), 7.82~7.72 (m, 6H), 7.62 (d, J=6.4 Hz, 2H), 7.06 (d, J=6.4 Hz, 2H); $^{19}$F NMR (376 MHz, $d_6$-DMSO, 298K), δ (ppm): −58.00 (s, 6F); MS (FAB, $^{102}$Ru): m/z 870 (M)$^+$. The element analysis data is: C, 51.24; N, 12.33; H, 2.94.

Examples 2 to 5 and Comparative Examples 1 and 2

The procedure for preparing each of the six-coordinated ruthenium complexes of Examples 2 to 5 and Comparative Examples 1 and 2 was similar to that of Example 1, except for the reactants and the eluent. The reactants, the eluents, and yields for the examples and comparative examples are shown in Table 1.

Example 6

The product of Preparation 14 (0.09 mmol), the product of Preparation 12 (0.18 mmol) and potassium acetate (0.46 mmol) were disposed in a 50 ml single neck bottle, followed by adding xylene (20 ml) and heating under reflux for 5 hours. After the reaction was finished, xylene was removed, and the reaction mixture was subjected to partition extraction three times using $CH_2Cl_2$ (50 ml) and deionized water (50 ml). A collected organic layer was added with anhydrous sodium sulfate to remove water, followed by filtration to obtain a filtrate. $CH_2Cl_2$ was removed from the filtrate by means of reduced pressure distillation to obtain a distilled mixture. The distilled mixture was subjected to column chromatography using an eluent of EA and $CH_2Cl_2$ (EA: $CH_2Cl_2$=1:3). A black solid product was obtained (52 mg, 39% yield).

The black solid product (52 mg, 0.035 mmol) was dissolved in acetone (20 ml), followed by adding sodium hydroxide solution (0.2 ml, 1M) and heating under reflux for 4 hours. After the reaction was finished, acetone was removed and deionized water was added into the reaction mixture. Thereafter, pH of the reaction mixture was adjusted to 3 using hydrogen chloride (2N) so as to precipitate a solid product. The solid product was collected by centrifugation, followed by washing several times with deionized water, acetone and diethyl ether, thereby obtaining a dark reddish brown solid product (44 mg, 88% yield).

The spectrum analysis for the dark reddish brown solid product is: $^1$H NMR (400 MHz, $d_6$-DMSO, 298K), δ (ppm): 8.98 (s, 2H), 8.75 (d, J=8.8 Hz, 2H), 8.02 (d, J=6 Hz, 2H), 7.75~7.78 (m, 6H), 7.58 (d, J=7.2 Hz, 2H), 7.43 (d, J=6.8 Hz, 2H), 7.16 (d, J=8.4 Hz, 8H), 6.97 (d, J=6.8 Hz, 2H), 6.77 (d, J=8.4 Hz, 8H), 1.17 (s, 36H); $^{19}$F NMR (376 MHz, $d_6$-DMSO, 298K), δ(ppm): −58.07 (s, 6F); MS (FAB, $^{102}$Ru): m/z 1428.5 (M)$^+$.

Example 7

The product of Preparation 14 (0.09 mmol), the product of Preparation 13 (0.18 mmol) and potassium acetate (0.46 mmol) were disposed in a 50 ml single neck bottle, followed by adding xylene (20 ml) and heating under reflux for 5 hours. After the reaction was finished, xylene was removed, and the reaction mixture was subjected to partition extraction three times using $CH_2Cl_2$ (50 ml) and deionized water (50 ml). A collected organic layer was added with anhydrous sodium sulfate to remove water, followed by filtration to obtain a filtrate. $CH_2Cl_2$ was removed from the filtrate by means of reduced pressure distillation to obtain a distilled mixture. The distilled mixture was subjected to column chromatography using an eluent of EA and hexane (EA: hexane=1:3). A black solid product was obtained (52 mg, 40% yield).

The black solid product (0.035 mmol) was dissolved in acetone (20 ml), followed by adding sodium hydroxide solution (0.2 ml, 1M) and heating under reflux for 4 hours. After the reaction was finished, acetone was removed and deionized water was added into the reaction mixture. Thereafter, pH of the reaction mixture was adjusted to 3 using hydrogen chloride (2N) so as to precipitate a solid product. The solid product was collected by centrifugation, followed by washing several times with deionized water, acetone and diethyl ether, thereby obtaining a dark reddish brown solid product (90% yield).

The spectrum analysis for the dark reddish brown solid product is: $^1$H NMR (400 MHz, $d_6$-DMSO, 298K), δ (ppm): 8.92 (s, 2H), 8.17 (d, J=8.8 Hz, 2H), 7.90 (d, J=6 Hz, 2H), 7.76 (t, J=8 Hz, 2H), 7.71 (d, J=6 Hz, 2H), 7.70 (s, 2H), 7.55 (d, J=7.6 Hz, 2H), 7.30 (d, J=6.8 Hz, 2H), 7.18 (d, J=8.4 Hz, 8H), 6.98 (d, J=6.8 Hz, 2H), 6.79 (d, J=8.4 Hz, 8H), 1.18 (s, 36H); $^{19}$F NMR (376 MHz, $d_6$-DMSO, 298K), δ(ppm): −79.90 (t, J=9 Hz, 3F), −107.47 (d, J=27, 2F), −127.09 (d, J=23 Hz, 2F); MS (FAB, 102Ru): m/z 1628.5 (M)$^+$.

Example 8

The product of Preparation 14 (0.111 mmol), the product of Preparation 8 (0.227 mmol) and potassium acetate (0.824 mmol) were disposed in a 50 ml single neck bottle, followed by adding xylene (20 ml) and heating under reflux for 5 hours. After the reaction was finished, xylene was removed, and the reaction mixture was subjected to partition extraction three times using $CH_2Cl_2$ (50 ml) and deionized water (50 ml). A collected organic layer was added with anhydrous sodium sulfate to remove water, followed by filtration to obtain a filtrate. $CH_2Cl_2$ was removed from the filtrate by means of reduced pressure distillation to obtain a distilled mixture. The distilled mixture was subjected to column chromatography using an eluent of EA and hexane (EA: hexane=1:3). A black solid product was obtained (42 mg, 20% yield).

The black solid product (0.0425 mmol) was dissolved in acetone (20 ml), followed by adding sodium hydroxide solution (0.2 ml, 1M) and heating under reflux for 3 hours. After the reaction was finished, acetone was removed and deionized water was added into the reaction mixture. Thereafter, pH of the reaction mixture was adjusted to 3 using hydrogen chloride (2N) so as to precipitate a solid product. The solid product was collected by centrifugation, followed by washing several times with deionized water, acetone and diethyl ether, thereby obtaining a dark brown solid product (30 mg, 78% yield).

The spectrum analysis for the dark brown solid product is: $^1$H NMR (400 MHz, $d_6$-DMSO, 298K), δ (ppm): 8.90 (s, 4H), 8.10 (d, J=6.0 Hz, 2H), 7.82~7.78 (m, 6H), 7.70~7.67 (m, 4H), 7.12 (d, J=6.8 Hz, 2H), 7.06 (d, J=3.2 Hz, 2H), 6.84 (d, J=3.6 Hz, 2H), 2.76~2.68 (m, 4H), 1.50~1.47 (m, 4H), 1.21~1.14 (m, 12H), 0.79 (t, J=6.7 Hz, 6H); $^{19}$F NMR (376 MHz, d6-DMSO, 298K), δ (ppm): −58.16 (s, 6F); MS (FAB, $^{102}$Ru): m/z 1202 (M+1)$^+$. The element analysis data is: C, 57.94; N, 9.32; H, 4.19.

Examples 9 to 11

The procedure for preparing each of the six-coordinated ruthenium complexes of Examples 9 to 11 was similar to that of Example 8, except for the reactants and the eluent. The reactants, the eluents, and yields for Examples 9-11 are shown in Table 1.

Comparative Example 3

The six-coordinated ruthenium complexes in Comparative Example 3 has the structure of formula (o) in US Patent Application Publication No. 2011/0277841 A1 and was prepared based on the method disclosed in the US Patent Application Publication.

TABLE 1

| Six-coordinated ruthenium complex | | Preparation | Eluent for column chromatography | Color of product | Yield (%) |
|---|---|---|---|---|---|
| Example | 1 | 1 | 14 | EA:$CH_2Cl_2$ = 1:20 | dark brown | 87 |
|  | 2 | 2 | 14 | EA:hexane = 1:2 | black | 89 |
|  | 3 | 5 | 14 | EA:$CH_2Cl_2$ = 1:50 | dark brown | 89 |
|  | 4 | 6 | 14 | EA:$CH_2Cl_2$ = 1:50 | dark brown | 87 |
|  | 5 | 7 | 14 | EA:$CH_2Cl_2$ = 1:50 | dark brown | 88 |
|  | 6 | 12 | 14 | EA:hexane = 1:3 | dark reddish brown | 88 |
|  | 7 | 13 | 14 | EA:hexane = 1:3 | dark reddish brown | 90 |
|  | 8 | 8 | 14 | EA:hexane = 1:3 | dark brown | 78 |
|  | 9 | 9 | 14 | EA:hexane = 1:3 | black | 89 |
|  | 10 | 11 | 14 | EA:hexane = 1:2 | black | 89 |
|  | 11 | 10 | 14 | EA:hexane = 1:2 | black | 85 |
| Comparative Example | 1 | 3 | 14 | EA:$CH_2Cl_2$ = 1:20 | dark brown | 92 |
|  | 2 | 4 | 14 | EA:hexane = 1:1 | black | 92 |

The chemical structures of the six-coordinated ruthenium complexes of Examples 1 to 11 and Comparative Examples 1 and 2 are shown in Table 2.

TABLE 2

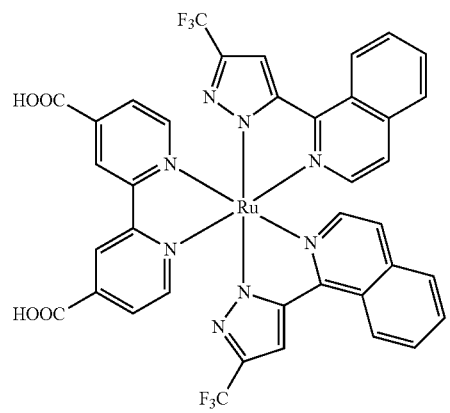

Example 1

TABLE 2-continued
| | |
|---|---|
| 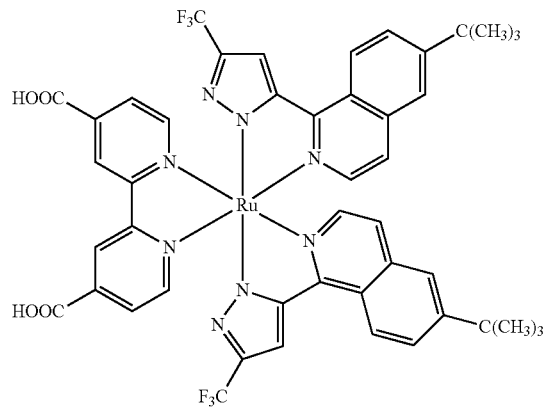 | Example 2 |
| 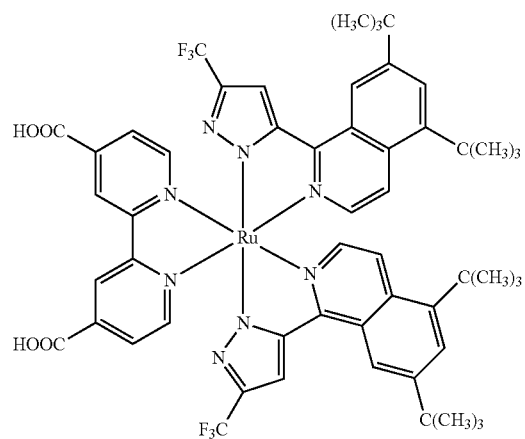 | Example 3 |
| 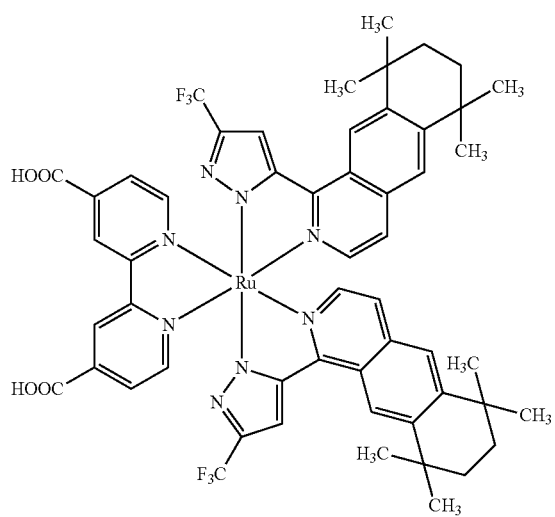 | Example 4 |

TABLE 2-continued
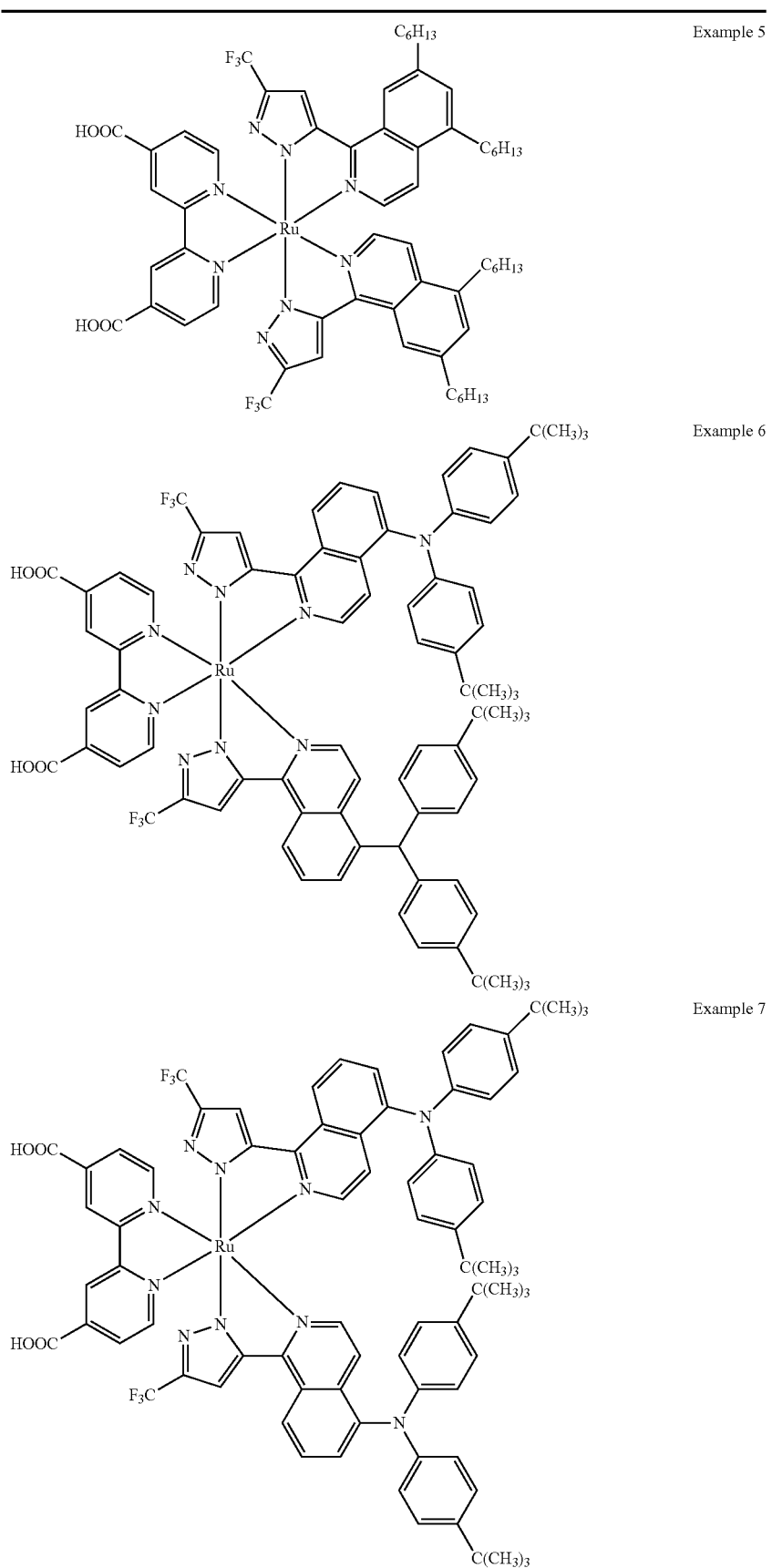
Example 5
Example 6
Example 7

TABLE 2-continued
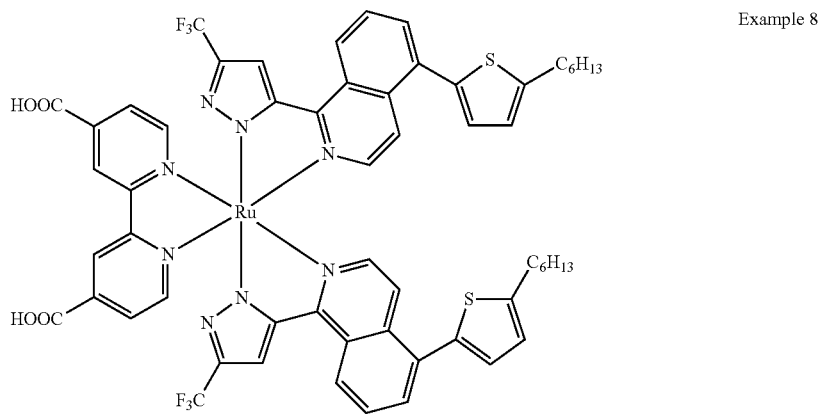
Example 8
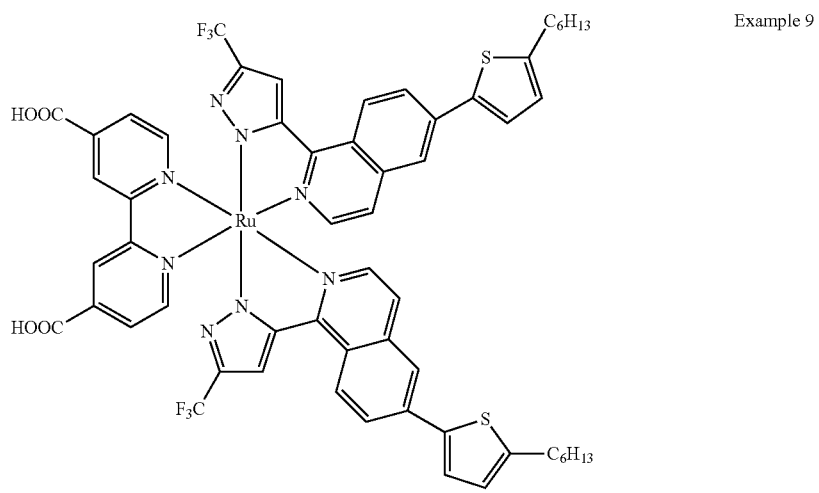
Example 9
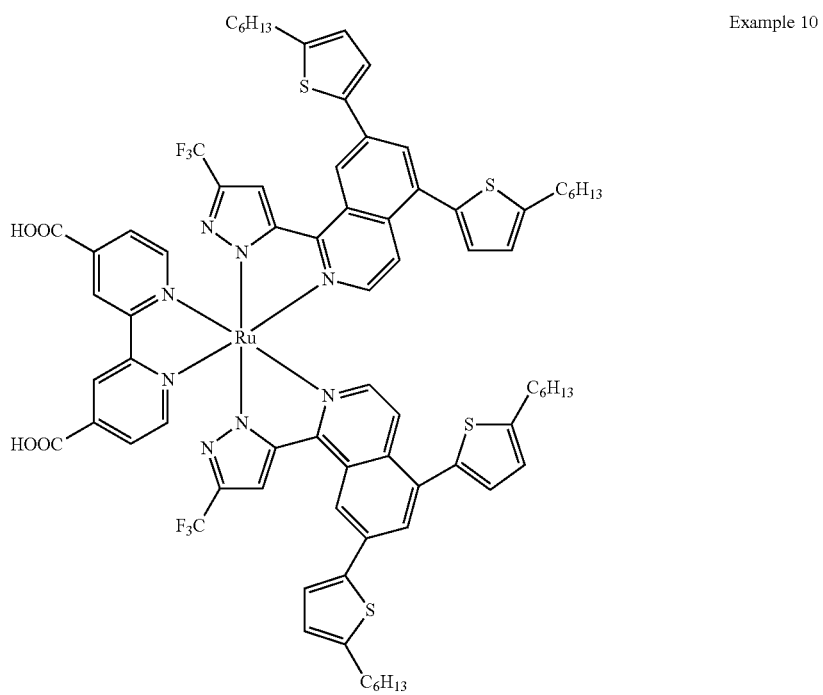
Example 10

TABLE 2-continued

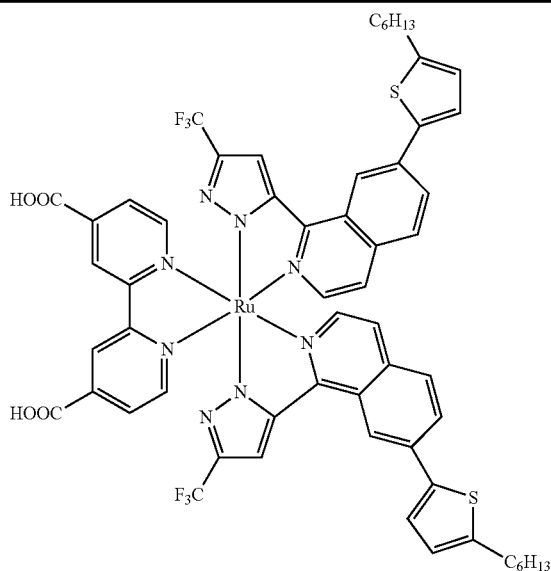

Example 11

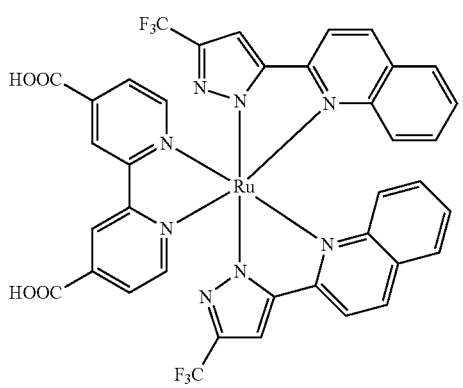

Comparative Example 1

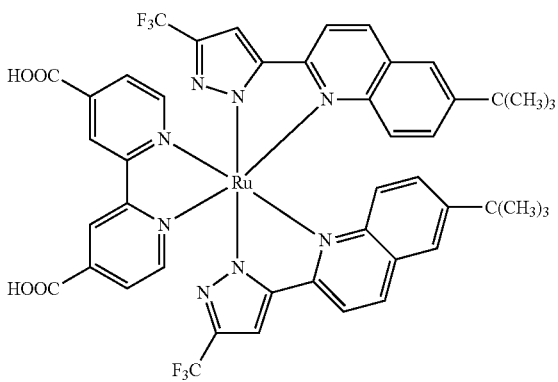

Comparative Example 2

The structural analysis data for NMR of Examples 2 to 5, Examples 9 to 11 and Comparative Examples 1 and 2 are as follows:

Example 2

The spectrum analysis for the product is: $^1$H NMR (400 MHz, $d_6$-DMSO, 298K), δ(ppm): 8.99 (s, 2H), 8.81 (d, J=9.2 Hz, 2H), 8.12 (d, J=5.6 Hz, 2H), 7.86 (dd, J=9.2, 2 Hz, 2H), 7.81 (d, J=2.0 Hz, 2H), 7.80 (s, 2H), 7.73 (dd, J=5.6, 2.0 Hz, 2H), 7.56 (d, J=6.4 Hz, 2H), 7.02 (d, J=6.4 Hz, 2H), 1.35 (s, 9H); $^{19}$F NMR (376 MHz, $d_6$-DMSO, 298K), δ (ppm): −58.00 (s, 6F); MS (FAB, $^{102}$Ru): m/z 982 (M)$^+$. The element analysis data is: C, 55.21; N, 11.44; H, 4.28.

Example 3

The spectrum analysis for the product is: $^1$H NMR (400 MHz, $d_6$-DMSO, 298K), δ(ppm): 8.96 (s, 2H), 8.56 (s, 2H), 8.04 (d, J=6.4 Hz, 2H), 8.00 (d, J=7.2 Hz, 2H), 7.82 (s, 2H), 7.75 (d, J=6.0 Hz, 2H), 7.41 (s, 2H), 7.18 (d, J=6.8 Hz, 2H), 1.49 (s, 18H), 1.44 (s, 18H); $^{19}$F NMR (376 MHz, d$_6$-DMSO, 298K), δ (ppm): −58.04 (s, 6F); MS (FAB, $^{102}$Ru): m/z 1095 (M+1)$^+$. The element analysis data is: C, 57.71; N, 10.19; H, 5.03.

Example 4

The spectrum analysis for the product is: $^1$H NMR (400 MHz, d$_6$-DMSO, 298K), δ (ppm): 8.98 (s, 2H), 8.57 (s, 2H), 8.13 (d, J=6.0 Hz, 2H), 7.90 (s, 2H), 7.73 (d, J=6.0 Hz, 2H), 7.47 (d, J=5.6 Hz, 2H), 7.46 (s, 2H), 6.93 (d, J=6.4 Hz, 2H), 1.73 (s, 8H), 1.42 (s, 6H), 1.41 (s, 6H), 1.35 (s, 6H), 1.25 (s, 6H); $^{19}$F NMR (376 MHz, d$_6$-DMSO, 298K), δ (ppm): −58.06 (s, 6F); MS (FAB, $^{102}$Ru): m/z 1091 (M+1)$^+$. The element analysis data is: C, 57.57; N, 10.20; H, 4.93.

Example 5

The spectrum analysis for the product is: $^1$H NMR (400 MHz, d$_6$-DMSO, 298K), δ (ppm): 8.97 (s, 2H), 8.37 (s, 2H), 8.06 (d, J=5.9 Hz, 2H), 7.72 (d, J=5.6 Hz, 2H), 7.59 (d, J=6.7 Hz, 2H), 7.33 (s, 2H), 7.06 (d, J=6.6 Hz, 2H), 2.78~2.76 (m, 8H), 1.58 (t, J=6.6 Hz, 2H), 1.44 (t, J=6.8 Hz, 2H), 1.25~1.11 (m, 16H), 0.80 (t, J=6.8 Hz, 3H), 1.44 (t, J=6.6 Hz, 3H); $^{19}$F NMR (376 MHz, d$_6$-DMSO, 298K), δ (ppm): −57.90 (s, 6F); MS (FAB, $^{102}$Ru): m/z 1206 (M)$^+$.

Example 9

The spectrum analysis for the product is: $^1$H NMR (400 MHz, d$_6$-DMSO, 298K), δ (ppm): 8.92 (s, 2H), 8.83 (d, J=9.1 Hz, 2H), 8.11 (d, J=5.9 Hz, 2H), 8.04 (s, 2H), 7.93 (d, J=8.8 Hz, 2H), 7.81 (s, 2H), 7.71 (d, J=5.4 Hz, 2H), 7.58~7.55 (m, 4H), 7.04 (d, J=6.4 Hz, 2H), 6.90 (d, J=3.4 Hz, 2H), 2.79 (t, J=7.4 Hz, 4H), 1.64~1.57 (m, 4H), 1.31~1.25 (m, 12H), 0.83 (t, J=6.8 Hz, 6H); $^{19}$F NMR (376 MHz, d$_6$-DMSO, 298K), δ (ppm): −58.00 (s, 6F); MS (FAB, $^{102}$Ru): m/z 1202 (M+1)$^+$.

Example 10

The spectrum analysis for the product is: $^1$H NMR (400 MHz, d$_6$-DMSO, 298K), δ (ppm): 8.94 (s, 2H), 8.73 (s, 2H), 8.16 (J=5.6 Hz, 2H), 7.92 (s, 2H), 7.72 (d, J=5.6 Hz, 2H), 7.61 (d, J=6.4 Hz, 2H), 7.52~7.49 (m, 4H), 7.15 (d, J=6.0 Hz, 2H), 7.01 (s, 2H), 6.85 (d, J=13.6 Hz, 4H), 2.82~2.74 (m, 8H), 1.64~1.55 (m, 8H), 1.36-1.20 (m, 24H), 0.85~0.80 (m, 6H); MS (FAB, $^{102}$Ru): m/z 1202 (M+1)$^+$. The element analysis data is: C, 60.01; N, 7.11; H, 4.57.

Example 11

The spectrum analysis for the product is: $^1$H NMR (400 MHz, d$_6$-DMSO, 298K), δ(ppm): 8.95 (s, 2H), 8.72 (s, 2H), 8.07 (d, J=5.4 Hz, 4H), 7.94 (d, J=8.4 Hz, 2H), 7.73 (d, J=5.6 Hz, 2H), 7.63~7.55 (m, 6H), 7.05 (d, J=3.4 Hz, 2H), 6.93 (s, 2H), 2.82 (t, J=6.9 Hz, 4H), 1.65~1.61 (m, 4H), 1.33~1.27 (m, 12H), 0.84 (t, J=6.3 Hz, 6H); $^{19}$F NMR (376 MHz, d$_6$-DMSO, 298K), δ (ppm): −58.00 (s, 6F); MS (FAB, $^{102}$Ru): m/z 1202 (M+1)$^+$.

Comparative Example 1

The spectrum analysis for the product is: $^1$H NMR (400 MHz, d$_6$-DMSO, 298K), δ (ppm): 9.06 (s, 2H), 8.28 (d, J=6.0 Hz, 2H), 8.20 (d, J=8.4 Hz, 2H), 7.90 (d, J=8.4 Hz, 2H), 7.79 (d, J=7.6 Hz, 2H), 7.68 (d, J=6.0 Hz, 2H), 7.41 (s, 2H), 7.38 (t, J=7.6 Hz, 2H), 7.05 (t, J=7.6 Hz, 2H), 6.78 (d, J=8.8 Hz, 2H); $^{19}$F NMR (376 MHz, d$_6$-DMSO, 298K), δ (ppm): −58.07 (s, 6F); MS (FAB, $^{102}$Ru): m/z 871 (M+1)$^+$. The element analysis data is: C, 51.17; N, 12.16; H, 3.03.

Comparative Example 2

The spectrum analysis for the product is: $^1$H NMR (400 MHz, d$_6$-DMSO, 298K), δ (ppm): 9.00 (s, 2H), 8.27 (d, J=8.8 Hz, 2H), 8.11 (d, J=6.0 Hz, 2H), 8.00 (d, J=8.4 Hz, 2H), 7.78 (d, J=2.0 Hz, 2H), 7.68 (dd, J=6.0, 1.6 Hz, 2H), 7.46 (s, 2H), 7.08 (dd, J=9.2, 2.4 Hz, 2H), 6.69 (d, J=9.6 Hz, 2H), 1.24 (s, 9H); $^{19}$F NMR (376 MHz, d$_6$-DMSO, 298K), δ (ppm): −58.14 (s, 6F); MS (FAB, $^{102}$Ru): m/z 983 (M+1)$^+$. The element analysis data is: C, 54.13; N, 10.87; H, 4.16.

[Test]

1. Measurement of Molar Extinction Coefficient (Hereinafter Referred to as ε)

Each of the six-coordinated ruthenium complexes of Examples 1 to 11 and Comparative Examples 1 and 2 was dissolved in DMF, followed by measuring molar extinction coefficient thereof using a UV-Visible Spectrophotometer (Hitachi Spectrophotometer; Model no.: U-3900).

2. Measurement of Photoelectric Conversion Efficiency

It is noted that the manufacturing process of a dye-sensitized solar cell is well known in the art and the following examples are used for illustration, and should not be construed as limiting the implementation of the present invention.

To manufacture the dye-sensitized solar cell, a fluoride-doped tin oxide coated glass (15×15 mm$^2$, thickness: 3.2 mm, sheet resistance: 9 Ω/cm$^2$) was washed using a cleaning agent, water, acetone and ethanol, followed by placing in an ultra-violet ozone device for 15 minutes. Thereafter, titanium dioxide nanoparticles (20 nm) were applied on the fluoride-doped tin oxide coated glass by means of a screen printing process to achieve an applied surface area of 0.25 cm$^2$, followed by thermal cracking at 325° C. for 30 minutes, at 375° C. for 5 minutes, at 450° C. for 15 minutes, and at 500° C. for 3 minutes in sequence. After cooling, the fluoride-doped tin oxide coated glass applied with titanium dioxide nanoparticles was immersed in a titanium tetrachloride aqueous solution (40 mM) at 70° C. for 30 minutes and rinsed with water and ethanol, followed by thermal cracking at 500° C. for 30 minutes to form a conductive substrate containing titanium dioxide. After the conductive substrate was cooled to 80° C., the same was immersed in a dye solution (3×10$^{-4}$M) for 18 hours to form a first electrode. The dye solution contains the six-coordinated ruthenium complex of the examples and comparative examples, dimethyl sulfoxide (DMSO) and methanol (the volume ratio of DMSO to methanol is 0.25).

A H$_2$PtCl$_6$ solution in isopropanol (10 μl, 50 mM) was dropped onto each of seven fluoride-doped tin oxide coated glasses (15×15 mm$^2$), followed by thermal cracking at 400° C. for 15 minutes to obtain a second electrode.

Iodine and iodic ions were dissolved in a solvent containing valeronitrile and acetonitrile (v/v=15: 85) to form an electrolytic component.

The first and second electrodes were packaged in pairs using a hot melting polymer film, and the electrolytic component (10 μL) was injected into pre-drilled small holes in the second electrodes. Next, the small holes were sealed using the hot melting polymer film and small pieces of glass, thereby obtaining the dye-sensitized solar cells.

The dye-sensitized solar cells were covered with a light-shield plate of stainless steel but had an exposed irradiation area of 0.16 cm$^2$. The exposed irradiation area of each of the dye-sensitized solar cells was irradiated by a solar simulator (150 W xenon lamp; Class A, Newport Oriel; Model no.: 91159) that provides a simulation light with air mass (AM) 1.5 Global radiation and an intensity of 100 mW/cm². (The simulation light is defined by a standard solar cell with a KG-5 filter). An external voltage was applied to each of the dye-sensitized solar cells using a digital electrometer (Keithley; Model no.: 2400), and the short circuit current density thereof was recorded. Data were collected to plot a graph of voltage vs. short circuit current density. In this graph of voltage vs. current density, an open circuit voltage when a current density is 0 and a short circuit current density when a voltage is 0 were obtained to evaluate the photoelectric conversion efficiency (η). Specifically, the photoelectric conversion efficiency (η) is obtained by dividing the maximum value of the product of the open circuit voltage and the short circuit current density by the value of the incident light intensity.

TABLE 3

| Six-coordinated ruthenium complex | | UV absorption spectrum | | Short circuit current density (mA cm⁻²) | Open circuit voltage (mV) | Fill factor | η (%) |
|---|---|---|---|---|---|---|---|
| | | Wavelength (nm) | ε (×10³) | | | | |
| Example | 1 | 499 | 17 | 15.4 | 760 | 0.75 | 8.80 |
| | 2 | 495 | 16 | 16.3 | 860 | 0.72 | 10.1 |
| | 3 | 494 | 20 | 15.57 | 860 | 0.77 | 10.35 |
| | 4 | 504 | 19 | 16.27 | 850 | 0.77 | 10.58 |
| | 5 | 497 | 21 | 15.98 | 840 | 0.74 | 9.87 |
| | 6 | 507 | 23 | 15.7 | 850 | 0.72 | 9.63 |
| | 7 | 505 | 23 | 16.4 | 850 | 0.71 | 9.84 |
| | 8 | 509 | 23 | 15.03 | 850 | 0.77 | 9.79 |
| | 9 | 518 | 34 | 15.3 | 820 | 0.73 | 9.23 |
| | 10 | 520 | 36 | 14.22 | 830 | 0.78 | 9.21 |
| | 11 | 510 | 29 | 16.43 | 800 | 0.75 | 9.74 |
| Comparative Example | 1 | 500 | 12 | 14.6 | 780 | 0.73 | 8.36 |
| | 2 | 496 | 12 | 14.7 | 860 | 0.71 | 8.94 |
| | 3 | — | — | 12.7 | 830 | 0.74 | 7.84 |

From the experimental data in Table 3, it is revealed that the short circuit current densities and the photoelectric conversion efficiencies of the dye-sensitized solar cells of Examples 1 to 11 are 14.22 to 16.43 mAcm⁻² and 8.80 to 10.58%, respectively. However, the short circuit current densities and the photoelectric conversion efficiencies of the dye-sensitized solar cell that uses the photosensitized complex represented by Formula (o) in US Patent Application Publication No. 2011/0277841 A1 are 12.7 mAcm⁻² and 7.84%. Therefore, the six-coordinated ruthenium complex of this invention provides superior short circuit current density and photoelectric conversion efficiency for the dye-sensitized solar cell.

Compared to Comparative Examples 1 and 2, 1-(trifluoromethylpyrazole)-isoquinoline-based bidentate ligand that is used in Examples 1 to 5 of the present invention provides the dye-sensitized solar cell with improved short circuit current density and photoelectric conversion efficiency.

To sum up, the six-coordinated ruthenium complex of the present invention can absorb the light with a wavelength ranging from 400 to 600 nm, and could provide superior short circuit current density and photoelectric conversion efficiency for a dye-sensitized solar cell.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A six-coordinated ruthenium complex represented by the following formula (I):

RuL¹L²L³                                    (I)

wherein L¹ represents a 2,2'-bipyridine-based bidentate ligand having at least two functional groups selected from the group consisting of COOH, a carboxylate group and the combination thereof; and L² and L³ independently represent a 1-(haloalkylpyrazole)-isoquinoline-based bidentate ligand of formula (II) or formula (III);

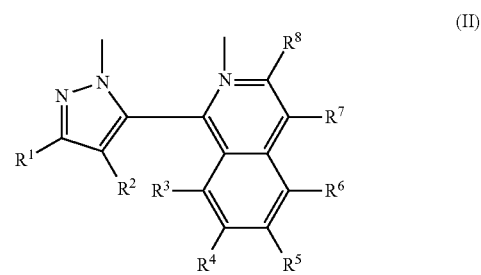

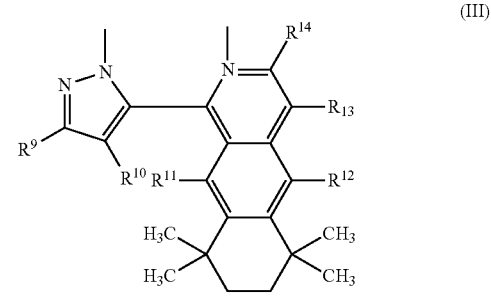

wherein R¹ and R⁹ represent a haloalkyl group; and R², R³, R⁴, R⁵, R⁶, R⁷, R⁸, R¹⁰, R¹¹, R¹², R¹³, and R¹⁴ independently represent hydrogen, an isobutyl group, a hexyl group,

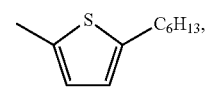

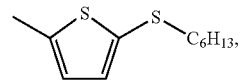

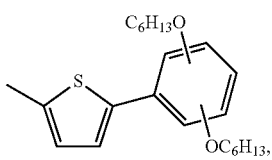

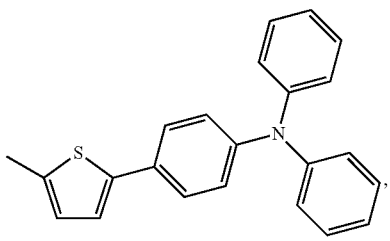 [SMILES: Cc1ccc(-c2ccc(N(c3ccccc3)c3ccccc3)cc2)s1]

or

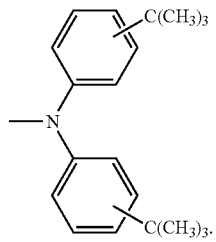

2. The six-coordinated ruthenium complex as claimed in claim 1, wherein $R^3$, $R^4$, $R^5$, $R^6$, $R^7$, and $R^8$ cannot be hydrogen at the same time.

3. The six-coordinated ruthenium complex as claimed in claim 1, wherein $R^{11}$, $R^{12}$, $R^{13}$, and $R^{14}$ cannot be hydrogen at the same time.

4. The six-coordinated ruthenium complex as claimed in claim 1, wherein $R^2$, $R^3$, $R^4$, $R^5$, $R^6$, $R^7$, $R^8$, $R^{10}$, $R^{11}$, $R^{12}$, $R^{13}$, and $R^{14}$ independently represent hydrogen, an isobutyl group, a hexyl group,

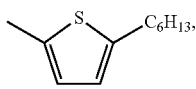

or

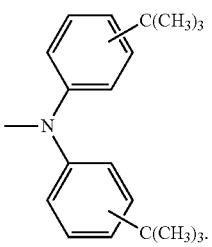

5. The six-coordinated ruthenium complex as claimed in claim 1, wherein $R^1$ and $R^9$ independently represent a $C_nF_{2n+1}$, and n represents an integer ranging from 1 to 7.

6. The six-coordinated ruthenium complex as claimed in claim 1, wherein said 2,2'-bipyridine-based bidentate ligand is represented by the following formula (IV):

(IV)

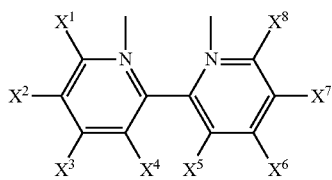

wherein $X^1$, $X^2$, $X^3$, $X^4$, $X^5$, $X^6$, $X^7$, and $X^8$ independently represent hydrogen, halogen, a trifluoromethyl group, a $C_1$ to $C_{12}$ linear alkyl group, a $C_1$ to $C_{12}$ branched alkyl group, a phosphoryl group, a phosphate group, a boric acid group, a borate group, a sulfo group, a sulfonate group, a carboxylate group or —COOH; with the proviso that at least two of $X^1$ to $X^8$ represent —COOH, the carboxylate group, or the combination thereof.

7. The six-coordinated ruthenium complex as claimed in claim 6, wherein $X^3$ and $X^6$ independently represent —COOH.

8. The six-coordinated ruthenium complex as claimed in claim 6, wherein $X^3$ and $X^6$ independently represent a carboxylate group.

9. The six-coordinated ruthenium complex as claimed in claim 8, wherein the carboxylate group is represented by —COOM, M being a metal ion.

\* \* \* \* \*